United States Patent
Miyahara et al.

(10) Patent No.: US 10,548,999 B2
(45) Date of Patent: Feb. 4, 2020

(54) METHOD AND APPARATUS FOR STERILIZING PREFORM

(71) Applicant: DAI NIPPON PRINTING CO., LTD., Tokyo (JP)

(72) Inventors: Yoshihiro Miyahara, Tokyo (JP); Hirotaka Tsuchiya, Tokyo (JP); Yoshio Nishida, Tokyo (JP)

(73) Assignee: Sai Nippon Printing Co., Ltd., Shinjuku-Ku (JP)

(*) Notice: Subject to any disclaimer, the term of this patent is extended or adjusted under 35 U.S.C. 154(b) by 228 days.

(21) Appl. No.: 14/384,697

(22) PCT Filed: Mar. 13, 2013

(86) PCT No.: PCT/JP2013/057016
§ 371 (c)(1),
(2) Date: Sep. 12, 2014

(87) PCT Pub. No.: WO2013/137321
PCT Pub. Date: Sep. 19, 2013

(65) Prior Publication Data
US 2015/0037205 A1 Feb. 5, 2015

(30) Foreign Application Priority Data

Mar. 14, 2012 (JP) .................................. 2012-057826
Mar. 14, 2012 (JP) .................................. 2012-057829
(Continued)

(51) Int. Cl.
*A61L 2/07* (2006.01)
*B65B 55/10* (2006.01)
(Continued)

(52) U.S. Cl.
CPC .................. *A61L 2/07* (2013.01); *A61L 2/06* (2013.01); *A61L 2/18* (2013.01); *A61L 2/186* (2013.01);
(Continued)

(58) Field of Classification Search
CPC ............................. A61L 12/07; B65B 55/027
(Continued)

(56) References Cited

U.S. PATENT DOCUMENTS 3,719,017 A * 3/1973 Karlson .................. B65B 55/18
53/431
7,186,374 B2 3/2007 Zelina et al.
(Continued)

FOREIGN PATENT DOCUMENTS

DE 20-2009-018258 8/2011
EP 2 394 950 12/2011
(Continued)

OTHER PUBLICATIONS

Machine translation of Document No. FR 2766169 A1 provided by espacenet.com: "Sterilization installation container preforms thermoplastic material," Jan. 22, 1999.*
(Continued)

*Primary Examiner* — Kevin Joyner
*Assistant Examiner* — Holly M Mull
(74) *Attorney, Agent, or Firm* — Burr & Brown, PLLC

(57) ABSTRACT

A preform is easily and speedily sterilized. A number of preforms (1), each having a bottomed tubular shape, are laid on a conveyer (4) in a scraggly overturned manner, these preforms passes inside a chamber (5) together with the conveyer, and hydrogen peroxide water mist is sprayed from both sides of the conveyer in a direction crossing the conveyer in the chamber, thereby adhering the sprayed hydrogen peroxide water to inner and outer surfaces of the preforms (1) on the conveyer (4).

7 Claims, 10 Drawing Sheets

(30) Foreign Application Priority Data

Sep. 5, 2012 (JP) .................................. 2012-195461
Sep. 5, 2012 (JP) .................................. 2012-195462

(51) Int. Cl.
| | | |
|---|---|---|
| A61L 2/18 | (2006.01) | |
| B65B 55/02 | (2006.01) | |
| A61L 2/06 | (2006.01) | |
| A61L 2/22 | (2006.01) | |
| A61L 2/20 | (2006.01) | |

(52) U.S. Cl.
CPC ............... *A61L 2/208* (2013.01); *A61L 2/22* (2013.01); *B65B 55/02* (2013.01); *B65B 55/10* (2013.01); *A61L 2202/23* (2013.01)

(58) Field of Classification Search
USPC .......................................................... 422/27
See application file for complete search history.

(56) References Cited

U.S. PATENT DOCUMENTS

| | | |
|---|---|---|
| 8,652,414 B2 | 2/2014 | Peter et al. |
| 2008/0107562 A1* | 5/2008 | Hayashi .................... A61L 2/06 422/28 |
| 2008/0283370 A1* | 11/2008 | Monti .................... B65B 21/04 198/867.01 |
| 2010/0170867 A1* | 7/2010 | Hayakawa ............ B67C 7/0073 215/379 |
| 2013/0061557 A1 | 3/2013 | Kitano et al. |
| 2015/0027088 A1 | 1/2015 | Miyahara et al. |

FOREIGN PATENT DOCUMENTS

| | | | |
|---|---|---|---|
| EP | 2465545 | 6/2012 | |
| EP | 2653395 | 10/2013 | |
| FR | 2766169 A1 * | 1/1999 | ............... A61L 2/18 |
| JP | 05-065148 | 3/1993 | |
| JP | 2000-326935 | 11/2000 | |
| JP | 2001-510104 | 7/2001 | |
| JP | 2007-111886 | 5/2007 | |
| JP | 2010-202284 | 9/2010 | |
| JP | 2012-021675 | 2/2012 | |
| WO | 02-064174 | 8/2002 | |
| WO | 2011/148953 | 12/2011 | |
| WO | 2013-137325 | 9/2013 | |

OTHER PUBLICATIONS

Oxonia Active MSDS provided by Ecolab Inc., Feb. 11, 2010, p. 1.*
International Search Report—PCT/JP2013/057016—May 14, 2013.

* cited by examiner

Fig 1
(A)
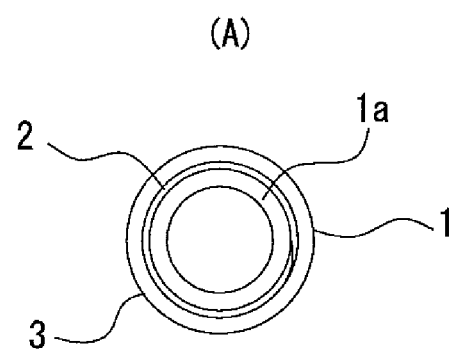
(B)
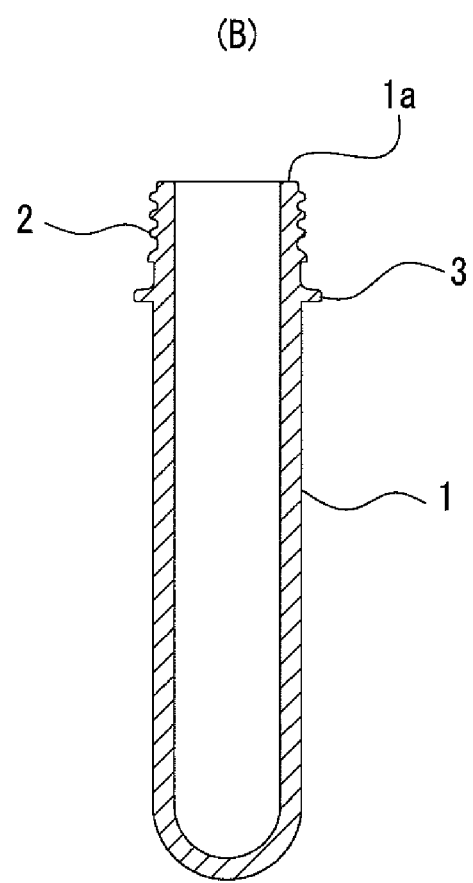

Fig 4

Fig 10
(A)
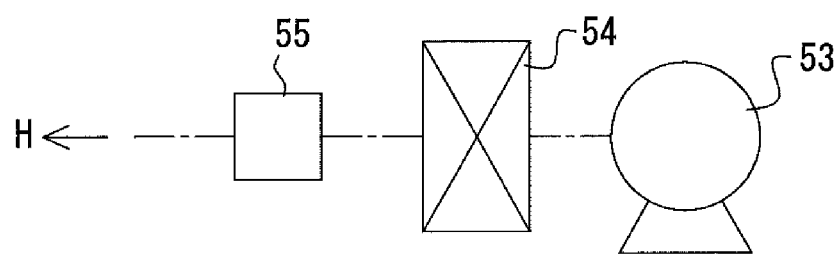
(B)
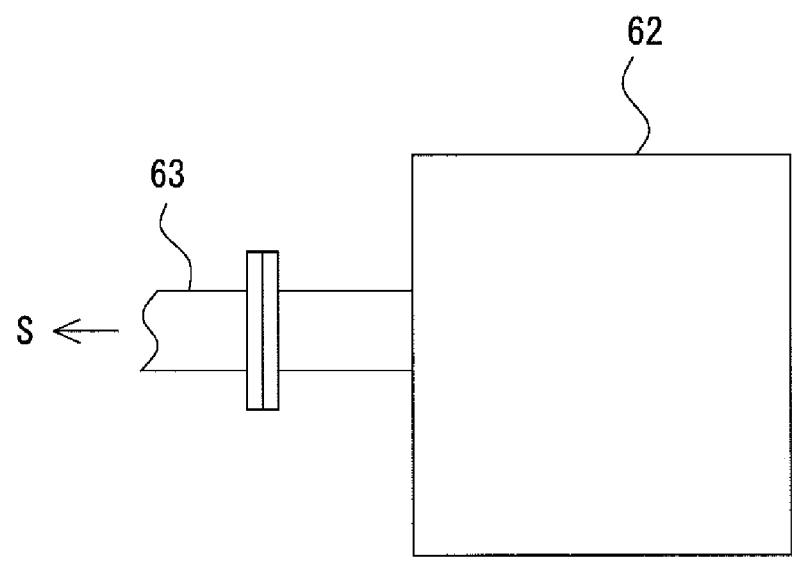

US 10,548,999 B2

METHOD AND APPARATUS FOR STERILIZING PREFORM

TECHNICAL FIELD

The present invention relates to a method and apparatus for sterilizing a preform for manufacturing a container such as bottle.

BACKGROUND TECHNOLOGY

In a conventional technology, in order to sterilize a bottle made of PET (polyethylene terephthalate) with hydrogen peroxide water, the bottle is guided into a chamber, the hydrogen peroxide water is sprayed within the chamber, and air is guided into the chamber to pass therethrough. According to such operation, even if the bottle has a complicated shape, mist of the hydrogen peroxide water uniformly adheres to a surface of the bottle to thereby uniformly sterilize the bottle surface (for example, refer to Patent Document 1).

Furthermore, it has been attempted to sterilize a preform in a preform stage before forming a bottle. That is, in a state in which a mouth portion of the preform is directed to a nozzle that is opened at a vertically downward of the preform mouth portion, a chemical agent such as hydrogen peroxide is jetted from the nozzle, the preform is thereafter guided into a heating furnace to thereby heat the preform to a temperature suitable for a blow molding process and enhance sterilizing effect, and thereafter, the preform is clamped by a forming mold and blow-molded into a bottle (for example, refer to Patent Document 2).

Furthermore, when the preform is sterilized in a preform stage, it has been attempted to put a number of preforms into which hydrogen peroxide water has been dropped respectively into a container, which is then sealed, and to sterilize inner and outer surfaces of these preforms with steam of the hydrogen peroxide water that is evaporated in the container at a time of transporting and maintaining the container. The preforms taken out from the container at a container receiving station is molded there into bottles in an aseptic state by a molding machine (for example, refer to Patent Document 3)

Still furthermore, there may be a case in which a use of sterilizing agent such as hydrogen peroxide or like is not desirable for sterilization of a preform. In such a case, as a method for sterilizing the preform with no use of the sterilizing agent, there has been provided a method in which water steam is blasted into to heat a preform to a temperature more than glass-transition point and maintain that temperature for a predetermined time for sterilizing the interior of the preform, and immediately thereafter, air is blasted into the preform to remove steam drain from the preform (for example, refer to Patent Document 4).

PRIOR ART DOCUMENT

Patent Document

Patent Document 1: Japanese Patent Laid-open Publication No. HEI 5-65148
Patent Document 2: Japanese Translation of PCT international Application Publication No. 2001-510104
Patent Document 3: Japanese Patent Laid-open Publication No. 2000-326935

Patent Document 4: Japanese Patent Laid-open Publication No. 2007-111886

SUMMARY OF THE INVENTION

Problems to be Solved by the Invention

It is required for a conventional method for sterilizing a bottle using hydrogen peroxide mist to miniaturize the hydrogen peroxide mist, which requires use of expensive mist generator, leading to cost up, thus being inconvenient.

Further, it is required for a method for jetting a chemical agent such as hydrogen peroxide or like to a preform to travel the preforms in a vertically elected and aligned state, and moreover, it is required to immediately guide the preforms after the adhesion of the chemical agent into a heating furnace. Because of this reason, a sterilization system is made complicated and is increased in size, leading to cost up for manufacture.

Furthermore, for a method for sterilizing a preform by dropping hydrogen peroxide solution into the preform, it is required to convey the preforms in an aligned state, and accordingly, it is difficult to deal with a number of preforms at a high speed. Moreover, since it is necessary to drop the hydrogen peroxide solution into each preform with a predetermined quantity, an expensive device for discharging the hydrogen peroxide solution while measuring the predetermined quantity is needed, thus being defective and disadvantageous.

Still furthermore, according to the conventional method in which the interior of the preform is sterilized using steam, a problem such that a sterilizing agent may remain is solved. However, if drain of the steam remains inside the preform, such remaining steam drain may cause a reason for generation of whitening at a time of molding the preform into a container, and hence, it is required to provide a process for removing the drain after the sterilization, thus providing a problem. In addition, when the steam is applied to the mouth portion of the preform for a long time, the mouth portion is liable to be deformed, which may cause a loss of sealing performance when a lid is applied to the mouth portion. Moreover, the sterilization only by the steam may cause a problem such that bacteria or like easily remains alive.

An object of the present invention is to solve the problem and/or inconvenience mentioned above.

Means for Solving the Problem

To achieve the above object, the present invention adopts the following configurations.

That is, the invention according to a first aspect adopts a method for sterilizing a preform, wherein a number of preforms (1), each having a bottomed tubular shape, are loaded on a conveyer (4) in a scraggly overturned manner, the preforms (1) pass through a chamber (5) together with the conveyer (4), and hydrogen peroxide water is sprayed within the chamber (5) from both sides of the conveyer (4) in a direction crossing the conveyer (4), thereby adhering the hydrogen peroxide water to inner and outer surfaces of each of the preforms (1) on the conveyer (4).

There is provided a method for sterilizing a preform wherein a number of preforms, each having a bottomed tubular shape, are loaded on a conveyer in a scraggly overturned manner, the preforms pass through a chamber together with the conveyer, hydrogen peroxide water is sprayed within the chamber from both sides of the conveyer in a direction crossing the conveyer to thereby adhere the hydrogen peroxide water to inner and outer surfaces of each of the preforms on the conveyer, and thereafter, superheated steam having a temperature of 200° C. to 500° C. made from water is blasted to at least the inner surface of all surfaces of the preform including a mouth portion thereof at a pressure more than atmospheric pressure.

As recited in a second aspect or a third aspect of the present invention, in the preform sterilizing method according to the first aspect of the present invention, it may be preferred that in the wherein the hydrogen peroxide water is atomized into mist by a two-fluid spray using pressurized air.

As recited in a fourth aspect of the present invention, in the preform sterilizing method according to any one of the first to third aspects of the present invention, it may be preferred that concentration of the hydrogen peroxide water is within 20% to 35%.

As recited in a fifth aspect of the present invention, in the preform sterilizing method according to any one of the third or fourth aspects of the present invention, it may be preferred that hot air having a temperature of 40° C. to 150° C. is mixed with the mist of the hydrogen peroxide water.

As recited in a sixth aspect of the present invention, in the preform sterilizing method according to any one of the first to fifth aspects of the present invention, it may be preferred that an interior of the chamber (5) is preliminarily sterilized by spraying the hydrogen peroxide water before starting the sterilization of the preform (1).

The invention according to a seventh aspect adopts an apparatus for sterilizing a preform comprising: a conveyer (4) on which a preform (1), having a bottomed tubular shape, is laid in an overturned manner; a chamber (5) provided to a horizontally traveling portion of the conveyer (4); and a spray nozzle (10) that sprays hydrogen peroxide water from both sides of the conveyer (4) in a direction crossing the conveyer (4) in the chamber so as to adhere the hydrogen peroxide water to inner and outer surfaces of the preform (1) on the conveyer (4).

The invention according to an eighth aspect adopts an apparatus for sterilizing a preform comprising: a conveyer (4) on which a preform (1), having a bottomed tubular shape, is laid in an overturned manner; a chamber (5) provided to a horizontally traveling portion of the conveyer (4); a spray nozzle (10) that sprays hydrogen peroxide water (M) from both sides of the conveyer (4) in a direction crossing the conveyer (4) in the chamber (5) so as to adhere the hydrogen peroxide water to inner and outer surfaces of the preform (1) on the conveyer (4); and a superheated steam supplying means that blasts superheated steam (S) having a temperature of 200° C. to 500° C. made from water is blasted to at least the inner surface of all surfaces of the preform (1) including a mouth portion (1a) thereof at a pressure more than atmospheric pressure while receiving the preform (1) discharged outside of the chamber (5) from the conveyer (4) and travelling the preform (1) in an elected posture.

The invention according to a ninth aspect adopts a method for sterilizing a preform wherein a number of preforms (1), each having a bottomed tubular shape, are loaded on a conveyer (4) in a scraggly overturned manner, the preforms (1) pass through a first chamber (5) by the conveyer (4), hot air (H) is sprayed during passing inside the first chamber (5) from both sides of the conveyer (4) in a direction crossing the conveyer (4) to thereby preheat the preform (1), and superheated steam (S) made from water is blasted toward the preform (1) from both sides of the conveyer (4), while passing the preforms (1) in a second chamber (6) to thereby sterilize the preforms (1).

As recited in a tenth aspect of the present invention, in the preform sterilizing method according to the ninth aspect of the present invention, it may be preferred that the preform (1) is preheated to a temperature of 40° C. to 70° C. by blasting the hot air (H).

As recited in an eleventh aspect of the present invention, in the preform sterilizing method according to the ninth aspect of the present invention, it may be preferred that the superheated steam (S) is produced by induction heating water mixed with the hydrogen peroxide.

The invention according to a twelfth aspect adopts an apparatus for sterilizing a preform comprising: a conveyer (4) on which a preform (1), having a bottomed tubular shape, is laid in an overturned manner; first and second chambers (5, 6) provided in series to a horizontally travelling portion of the conveyer (4); a preheating nozzle (11) that blasts hot air (H) from both sides of the conveyer (4) toward the preforms in the first chamber (5); and a sterilizing nozzle (20) that blasts superheated steam (S) made from water mixed with hydrogen peroxide from both sides of the conveyer (4) toward the preforms in the second chamber (6) to thereby sterilize the preforms (1).

The invention according to a thirteenth aspect adopts a method for sterilizing a preform wherein a number of preforms (1), each having a bottomed tubular shape, are loaded on a conveyer (4) in a scraggly overturned manner, the preforms (1) pass through a first chamber (5) by the conveyer (4), hot air (H) is blasted during passing inside the first chamber (5) from both sides of the conveyer (4) in a direction crossing the conveyer (4) to thereby preheat the preform (1), and superheated steam (S) is thereafter blasted toward the preforms (1) from both sides of the conveyer (4), while the preforms (1) passing in a second chamber (6) to thereby sterilize the preforms (1).

As recited in a fourteenth aspect of the present invention, in the preform sterilizing method according to the thirteenth aspect of the present invention, it may be preferred that the preform (1) is preheated to a temperature of 40° C. to 70° C. by blasting the hot air (H).

As recited in a fifteenth aspect of the present invention, in the preform sterilizing method according to the thirteenth aspect of the present invention, it may be preferred that the superheated steam (S) is produced by induction heating water mixed with the hydrogen peroxide.

The invention according to a sixteenth aspect adopts an apparatus for sterilizing a preform comprising: a conveyer (4) on which a preform (1), having a bottomed tubular shape, is laid in an overturned manner; first and second chambers (5, 6) provided in series to a horizontally travelling portion of the conveyer (4); a preheating nozzle (11) that blasts hot air (H) from both sides of the conveyer (4) toward the preforms (1) in the first chamber (5); and a sterilizing nozzle (20) that blasts superheated steam (S) from both sides of the conveyer (4) toward the preforms (1) in the second chamber (6) to thereby sterilize the preforms (1).

According to the invention of the first aspect, there is provided a method of sterilizing a preform wherein a number of preforms (1), each having a bottomed tubular shape, are loaded on a conveyer (4) in a scraggly overturned manner, the preforms (1) pass through a chamber (5) together with the conveyer (4), and hydrogen peroxide water is sprayed within the chamber (5) from both sides of the conveyer (4) in a direction crossing the conveyer (4), thereby adhering the hydrogen peroxide water to inner and outer surfaces of each of the preforms (1) on the conveyer (4). Accordingly, the preform (1) discharged from the preform molding machine is received by the conveyer (4) and the preform is then guided into the chamber (5) together with the conveyer (4) on which the preform (1) 1 is laid in the overturned state. Within the chamber (5), the hydrogen peroxide water is sprayed from both sides of the conveyer (4) in the direction crossing the conveyer, so that the mist of the hydrogen peroxide water adheres on the outer surface of the preform (1) on the conveyer (4). At this time, since the preform is overturned on the conveyer (4) by the vibration or like, the hydrogen peroxide water can uniformly adhere to the outer surface of the preform. Furthermore, the mist of the hydrogen peroxide water flows into the overturned preform through the mouth portion (1a) thereof to thereby also uniformly adhere to the inner surface of the preform (1). Thus, the entire surface of the preform (1) can be suitably sterilized by the hydrogen peroxide. In addition, as a result of adoption of the above invention, it is not necessary to use conventionally used preform aligning device and expensive hydrogen peroxide generator for discharging constant amount of the hydrogen peroxide water, and hence, a lot of preforms can be easily sterilized with reduced cost.

According to the invention of the second aspect, there is provided a method for sterilizing a preform wherein a number of preforms (1), each having a bottomed tubular shape, are loaded on a conveyer (4) in a scraggly overturned manner, the preforms (1) pass through a chamber (5) together with the conveyer (4), hydrogen peroxide water is sprayed within the chamber (5) from both sides of the conveyer (4) in a direction crossing the conveyer (4) to thereby adhere the hydrogen peroxide water to inner and outer surfaces of each of the preforms (1) on the conveyer (4), and thereafter, superheated steam (S) having a temperature of 200° C. to 500° C. made from water is blasted to at least the inner surface of all surfaces of the preform (1) including a mouth portion (1a) thereof at a pressure more than atmospheric pressure. Accordingly, the preform (1) discharged from the preform molding machine is received by the conveyer (4) and the preform is then guided into the chamber (5) together with the conveyer (4) on which the preform (1) 1 is laid in the overturned state. Within the chamber (5), the hydrogen peroxide water is sprayed from both sides of the conveyer (4) in the direction crossing the conveyer, so that the mist (M) of the hydrogen peroxide water adheres on the outer surface of the preform (1) on the conveyer (4). At this time, since the preform is overturned on the conveyer (4) by the vibration or like, the hydrogen peroxide water can uniformly adhere to the outer surface of the preform. Furthermore, the mist (M) of the hydrogen peroxide water flows into the overturned preform through the mouth portion (1a) thereof to thereby also uniformly adhere to the inner surface of the preform (1). Thus, the entire surface of the preform (1) can be suitably sterilized by the hydrogen peroxide. In a certain case in which the preforms (1) thus sterilized by the hydrogen peroxide is packaged and stored, and the package is thereafter delivered and opened, and then sent to the blow-molding machine or like, the superheated steam (S) is blasted at the time of being supplied to the blow-molding machine, so that the sterilization can be more surely performed, and thereafter is molded into a container by the blow-molding machine. In the meantime, in a case where the preform sterilized by the hydrogen peroxide is supplied as it is to the blow-molding machine or like, the preform is sterilized by the superheated steam (S) in a process of being transferred from the conveyer (4) to the blow-molding machine, so that the surely sterilized preform (1) is molded into a container (12) by the flow-molding machine.

In addition, as a result of adopting the above method of the present invention, it is not necessary to use conventionally used preform aligning device and expensive hydrogen peroxide generator for discharging constant amount of the hydrogen peroxide water, and hence, a lot of preforms can be easily sterilized with reduced cost.

According to the invention of the ninth aspect, the preform (1) discharged from the preform molding machine is received by the conveyer (4) and the preform is then guided into the first and second chambers (5, 6) together with the conveyer (4) on which the preform (1) 1 is laid in the overturned state. Within the second chamber (6), the superheated steam (S) is blasted from both sides of the conveyer (4), so that the outer surface of the preform (1) on the conveyer (4) can be suitably sterilized. In addition, at this time, since the preform is overturned on the conveyer (4) by the vibration or like, the superheated steam (S) can uniformly adhere to the outer surface of the preform. Furthermore, the superheated steam (S) flows into the overturned preform (1) through the mouth portion (1a) thereof to thereby also uniformly adhere to the inner surface of the preform (1). Thus, the entire surface of the preform (1) can be uniformly sterilized by the superheated steam (S).

Furthermore, since the superheated steam (S) is made from water mixed with the hydrogen peroxide, spore-forming bacteria can be also sterilized as well as general bacteria, fungus, yeast or like adhering to the surface of the preform (1).

Moreover, beforehand the sterilization by the blasting of the superheated steam (S), since the preform (1) is preheated in the first chamber (5) by blasting the hot air (H), even if using amount of the superheated steam (S) is reduced, desired sterilizing effect is attainable.

According to the invention of the thirteenth aspect, the preform (1) discharged from the preform molding machine is received by the conveyer (4) and the preform is then guided into the first and second chambers (5, 6) together with the conveyer (4) on which the preform (1) 1 is laid in the overturned state. Within the second chamber (6), the superheated steam (S) is blasted from both sides of the conveyer (4), so that the outer surface of the preform (1) on the conveyer (4) can be suitably sterilized. In addition, at this time, since the preform is overturned on the conveyer (4) by the vibration or like, the superheated steam (S) can uniformly adhere to the outer surface of the preform. Furthermore, the superheated steam (S) flows into the overturned preform (1) through the mouth portion (1a) thereof to thereby also uniformly adhere to the inner surface of the preform (1). Thus, the entire surface of the preform (1) can be uniformly sterilized by the superheated steam (S).

Moreover, beforehand the sterilization by the blasting of the superheated steam (S), since the preform (1) is preheated in the first chamber (5) by blasting the hot air (H), even if using amount of the superheated steam (S) is reduced, desired sterilizing effect is attainable.

BRIEF DESCRIPTION OF THE INVENTION

FIG. 1 represents one example of a preform capable of being sterilized by a sterilization method according to the present invention, in which (A) is a plan view and (B) is a front view.

FIG. 4 is an explanation view showing a method of sterilizing the preform with superheated steam.

FIG. 10 (A) is a block diagram of a hot air generating portion, and (B) is a block diagram of a superheated steam generating portion.

EMBODIMENT FOR CARRYING OUT THE INVENTION

Hereunder, embodiments for carrying out present invention will be described.

Embodiment 1

A preform as an object to be sterilized by the present invention is formed by injection molding a PET into a test-tube like bottomed tubular member. The preform is thereafter formed into a bottle having a desired shape (see FIG. 6 (B)), and as shown in FIGS. 1(A) and (B), a preform 1 is formed with a mouth portion 1a having a shape similar to that of a bottle after the molding at an initial time for the molding. A male screw portion 2 is formed on an outer peripheral surface of the mouth portion 1a at the same time as the time of molding the preform 1. The male screw portion 2 is engageable with a female screw portion of a cap, not shown, to be applied to the mouth portion 1a of the bottle. Below the male screw portion 2, a support ring 3 utilized at a time of filling drink in a bottle is formed.

Figure 2:
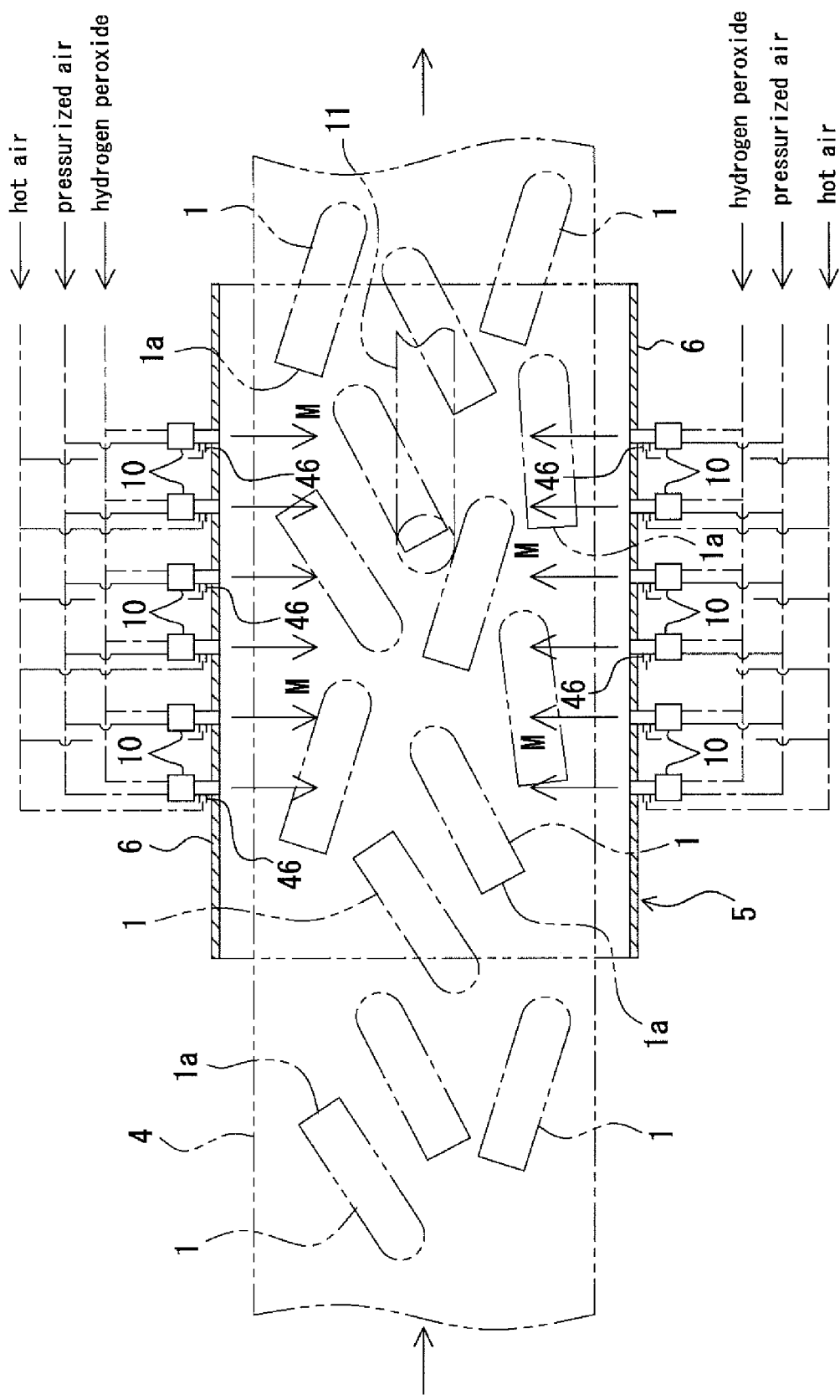
FIG. 2 is a partially cut-off plan view schematically showing an apparatus for carrying out a method of sterilizing a preform with hydrogen peroxide.
Figure 3:
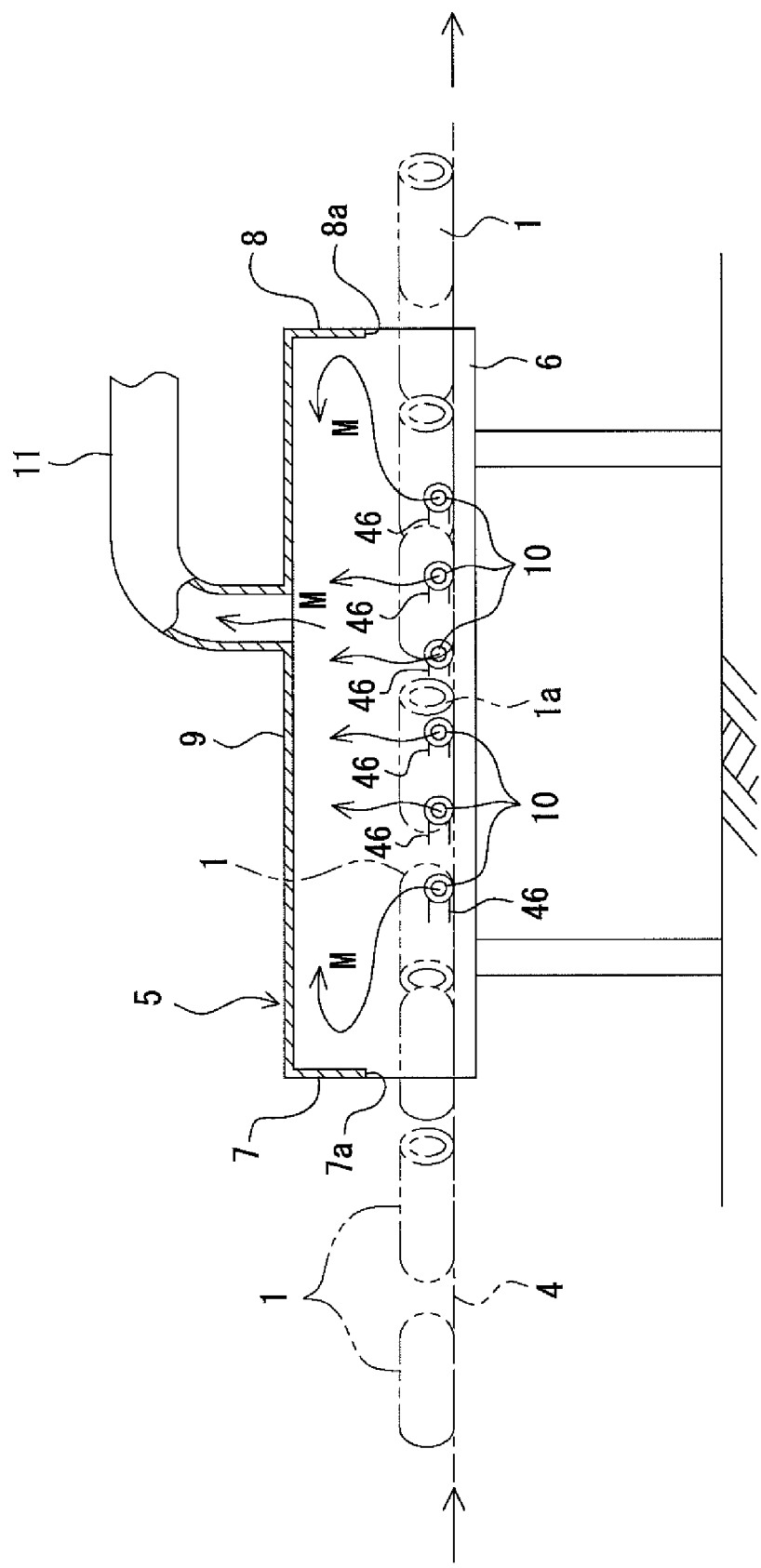
FIG. 3 is a vertical sectional view showing a schematic structure of the apparatus mentioned above.

An apparatus for sterilizing such preform 1 has a structure represented by FIGS. 2 and 3.

In FIGS. 2 and 3, reference numeral 4 denotes a belt-type conveyer. A preform molding machine, not shown, is arranged on an upstream side in the travelling direction shown with arrow of the conveyer 4. The molded preform 1 released from the preform molding machine is received by a hopper or like, not shown, on an upstream side of the conveyer 4. As shown in FIG. 2, the molded preforms 1 are laid on the conveyer in a scraggly overturned posture.

A middle section of the conveyer 4 can be traveled in the horizontal direction, and a chamber member 5 is applied in form of hood to this middle section of the conveyer 4.

The chamber member 5 is composed of both side wall sections 6 disposed so as to sandwich the conveyer 4 from both sides, front and rear wall sections 7, 8 disposed at front and rear end portions of the side wall sections 6, and a top wall section 9 disposed so as to shield the upper sides of the both side wall sections 6 and the front and rear wall sections 7, 8. The chamber member 5 may be called merely chamber 5 hereinafter.

Spray nozzles 10, that spray the hydrogen peroxide water in a direction crossing the conveyer 4 from the side edge sides thereof, are mounted to both the side wall sections 6, respectively. Although the spray nozzles 10 may be mounted one by one to both the side wall sections 6, it is preferred to arrange plural number of the spray nozzles 10 are arranged to both the side wall sections 6 along the travelling direction of the conveyer 4.

Moreover, as the spray nozzles 10, it is desirable to adopt two-fluid nozzles, in which the hydrogen peroxide water is supplied from one fluid path of the respective nozzles 10 and pressurized air is also supplied from the other one fluid path thereof.

When the pressurized air flows within the two-fluid spray nozzle 10 at high speed, the hydrogen peroxide water is taken up by the pressurized air to thereby form hydrogen peroxide mist, which is then discharged into the chamber 5 from the tip end of each spray nozzle 10. This hydrogen peroxide mist is sprayed and adheres to the surface of the preform 1 now travelling on the conveyer 4.

It may be possible to spray mixture of such hydrogen peroxide mist and hot air (heated air) having temperature of 40 to 150° C. to the preform 1.

With reference to FIGS. 2 and 3, reference numeral 46 demotes a nozzle that jets such hot air. The hot air jetted from this nozzle 46 is mixed with the mist of the hydrogen peroxide water generated by the two-fluid spray nozzle 10 and the mixture then flows toward the preform 1 while heating the mist. By heating the mist, the sterilizing effect can be enhanced.

The mist of the hydrogen peroxide water is discharged in the direction crossing the conveyer 4 from both sides of the conveyer 4 within the chamber 5, and the preform 1 is overturned on the conveyer 4 by vibration or like, so that the hydrogen peroxide water can uniformly adheres to the outer surface of the preform. At the same time, the hydrogen peroxide mist flows into the horizontally overturned preform 1 through the mouth portion 1a thereof to thereby also uniformly adhere to the inner surface of the preform 1. Furthermore, since the hydrogen peroxide mist discharged from the two-fluid spray nozzle 10 fills the interior of the chamber 5 and circulates therein, the circulated mist also uniformly adheres to the surface of the preform 1. According to this manner, the entire surface of the preform 1 can be suitably sterilized by the hydrogen peroxide.

It is preferred for the hydrogen peroxide used for the sterilization of the preform 1 to have concentration of 20 to 35%. In the case of the concentration being less than 20%, there may cause a case where spore-forming bacteria remains alive which may lead to defective sterilization, and on the other hand, in the case of the concentration being more than 35%, much amount of the hydrogen peroxide may remain on the preform.

Further, it is preferred that the hot air of temperature of 40 to 150° C. is mixed with the mist. In the case of the temperature being less than 40° C., the sterilization may become defective, and on the other hand, in the case of the temperature being more than 150° C., there likely causes a case of the preform being deformed.

The front and rear wall sections 7 and 8 of the chamber 5 are formed with openings 7a and 8a through which the conveyer 4, on which the preform 1 is placed, can pass. The top wall section 9 is connected to an exhaust duct 11. The mist of the hydrogen peroxide discharged into the chamber 5 is sucked into the exhaust duct by driving a blower, not shown, and then flows toward a recovery device. According to the operation mentioned above, the hydrogen peroxide mist is prevented from flowing out of the chamber 5 through the openings 7a and 8a formed to the front and rear wall sections 7 and 8 and the like.

The downstream side of the conveyer 4 than the chamber 5 extends toward a large-sized container or like, not shown. The preform 1 to which the hydrogen peroxide mist adheres within the chamber 5 is conveyed toward and into the large-sized container. The container is closed and sealed after predetermined numbers of the preforms 1 are loaded, stored and then transferred to a factory at which the preform 1 is molded into a bottle. During such storing and transferring of the preforms 1, the preforms 1 are sterilized by the hydrogen peroxide which is also trapped in the container.

Further, in an arrangement in which the downstream side of the conveyer 4 than the chamber 5 is connected to a blow-molding machine, the sterilized preform 1 is directly subjected to the blow-molding treatment so as to form a container such as bottle. Moreover, in an arrangement in which the blow-molding machine is connected to a content filling machine, the content such as drink fills the container such as bottle, the bottle is sealed and then discharged as aseptic packaged product in which the content fills.

Hereunder, function of the preform sterilization apparatus mentioned above will be explained together with a preform sterilization method.

Beforehand the starting of the sterilization treatment of the preform 1, the hydrogen peroxide water is preliminarily sprayed into the chamber 5 from the spray nozzle 10 to thereby sterilize the interior of the chamber 5.

By driving the preform molding machine, the molded preforms 1 are put on the upstream side of the travelling conveyer 4. The preforms 1 released from the preform molding machine are received on the upstream side portion of the conveyer 4, and as shown in FIG. 2, the preforms are laid on the conveyer 4 in a scraggly appearance.

The preforms 1 on the conveyer 4 enter the chamber 5 together with the conveyer 4 and are sprayed with the hydrogen peroxide water through the spray nozzle 10.

The hot air to be jetted from the nozzle 46 is mixed, as occasion demands, with the sprayed mist of the hydrogen peroxide water.

The hydrogen peroxide mist is discharged from both the sides of the conveyer in the direction crossing the conveyer 4 within the chamber 5. Further, since the preform 1 is overturned on the conveyer by vibration or like, the hydrogen peroxide water can uniformly adheres to the outer surface of the preform 1.

The hydrogen peroxide mist flows into the interior of the horizontally laying preform 1 through the mouth portion 1a of the preform 1 to thereby uniformly adhere to the inner surface thereof.

Further, since the hydrogen peroxide mist discharged through the spray nozzle 10 fills the chamber 5 and circulates therein, the mist also uniformly adheres, while flowing, to the surface of the preform 1, thus the entire surface of the preform 1 being uniformly sterilized by the hydrogen peroxide.

The preform 1 passes through the chamber 5 together with the conveyer 4 while being blasted with the hydrogen peroxide mist and is put into the large-sized container or like, and otherwise, the preform 1 is conveyed to the blow-molding machine and the filling machine without being loaded into the large-sized container, and is then discharged as an aseptic packaged product.

It is further to be noted that the present invention is not limited to the described embodiment, and other various embodiments or modes may be adopted as examples for embodiment.

Example 1

Mist of hydrogen peroxide water was produced by supplying hydrogen peroxide water of 35% concentration and pressurized air to a two-fluid spray, the thus produced mist was mixed with hot air having temperature of 60° C., and then, the mist of the hydrogen peroxide water was sprayed inside a chamber through a nozzle. The chamber is a box-shaped member, having no bottom, having a size of 1,000 mm width, 1,500 mm length and 200 mm height, and the box-shaped chamber was set to a predetermined position on the conveyer having 600 mm width. Preforms of the number of 860 bottles/min., each being formed into a bottle of 500 mm, were supplied to the conveyer, which is driven at a speed of 0.2/sec. At this time, the hydrogen peroxide water of amount of about 50 mg adhered to each preform.

The sterilizing power was evaluated with the *BaciLLus subtiLis* being indicator fungus, 4.2 D and 5.3 D were obtained with respect to the inner surface of the preform and the outer surface thereof, respectively.

Further, when such preform as mentioned above was molded into a bottle and water filled the bottle, remaining amount of the hydrogen peroxide was measured. The remaining amount thereof was 0.012 ppm.

Embodiment 2

Hereunder, an embodiment 2 of the present invention will be described.

A preform as an object of the present invention to which sterilization is performed is the same as that of the first embodiment 1 described hereinbefore.

Furthermore, an apparatus for sterilizing the preform 1 has the same structure as that of the first embodiment 1. The preform 1 to which the mist M of the hydrogen peroxide water adheres within the camber 5 is conveyed to and loaded into a large-sized container by the conveyer 4. The large-sized container into which the preforms of the predetermined numbers are accommodated is thereafter sealed, stored therein and then transferred to a factory at which the preform is molded into a bottle. During such storing and transferring of the preforms 1, the preforms 1 are sterilized by the hydrogen peroxide which is also trapped in the container.

The large-sized container is transferred to another factory at which package is opened, and the preforms 1 taken out therefrom are subjected to treatment described hereinafter, and then, formed into a product package in an aseptic state (see FIG. 6(F)).

Figure 4:
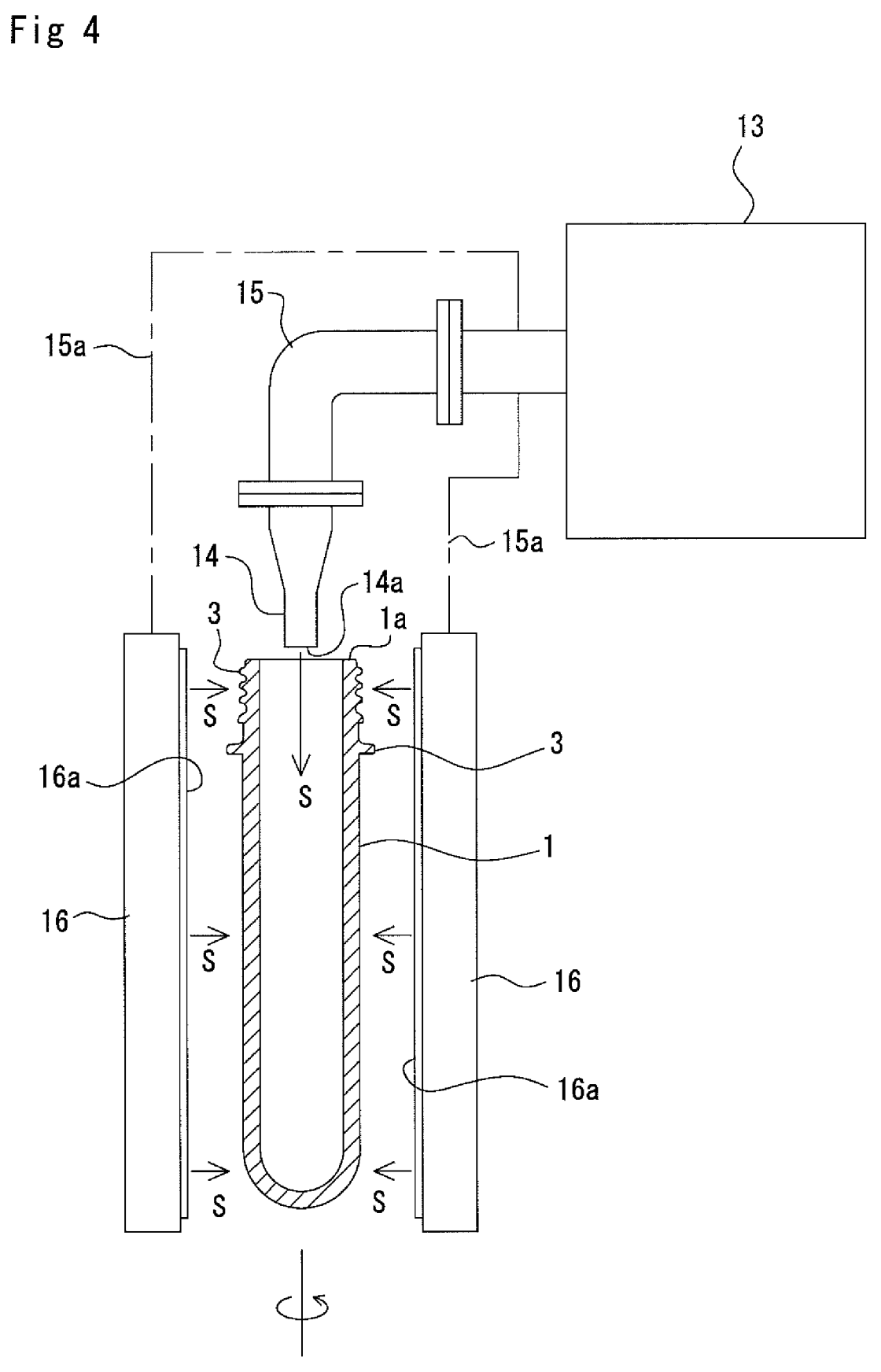

As shown in FIG. 4, the further sterilization of the preform 1 that has been already sterilized by the hydrogen peroxide is performed by blasting superheated steam S, having temperature of 200 to 500° C. and substantially atmospheric pressure, generated from water to the entire inner and outer surfaces of the preform 1 including the mouth portion 1a thereof.

It is preferred that the superheated steam to be blasted to the preform has a temperature of 200 to 500° C., and more preferably, 250 to 400° C. In the case of the temperature range within 200 to 500° C., only the surface of the preform is exposed to high heat temperature to thereby spore-forming bacteria adhering to the surface of the preform can be sterilized for a short time. In a case of less than 200° C., it is required for the preform to be blasted with the superheated steam for a long time for the sufficient sterilization, which leads to highly increased temperature to a PET forming the preform, and the preform is liable to be deformed. On the other hand, in a case of more than 500° C., the PET forming the preform is itself highly heated for a short time, which also leads to ready deformation of the preform.

The pressure of the superheated steam to be blasted to the preform is a pressure higher than atmospheric pressure, preferably of higher than 0.1 MPa and less than 0.3 MPa. In a case of near 0.1 MPa, even if the temperature is lowered in contact of the superheated steam to the preform, there is less possibility of condensation of the steam, but in the case of more than 0.3 MPa, the superheated steam blasted to the preform may be condensed (dewed) on the surface thereof. When the steam is condensed, there is a fear of generating whitening or like on the surface of a bottle at the time when the preform is blow-molded into the bottle.

Further, although the sterilization of the inner surface of the preform is essential, the sterilization of the outer surface may be performed by heating for the blow-molding treatment, that will be described hereinafter, or may be performed by adding further desired sterilization treatment after the flow-molding treatment.

The superheated steam S is obtainable by using a commercially sold superheated steam generator 13. More specifically, a superheated steam generator (UPSS (Trade Name of TOKUDEN Kabushiki Kaisha) may be used. This generator, though not shown, has a structure in which an induction heating coil is inserted into a central portion of a spiral of water-pass pipe composed of a spirally wound-up conductive member, water is guided into the water-pass pipe, and an AC voltage is applied to the induction heating coil. It may be possible to perform frequency-conversion of the AC voltage by an inverter so as to be energized. By the application of the AC voltage, the induction heating coil generates alternate magnetic flux, and an induced current passes the water-pass pipe, which is then heat-generated. The water passing inside the water-pass pipe is heated by this heat-generation and changed into saturated steam, which then becomes superheated steam S which is thereafter taken out of the water-pass pipe.

It is further to be noted that the induction heating coil may be formed from a conductive tube, and by passing water through this conductive tube, heating effect may be further enhanced.

As the superheated steam S, it is possible to obtain steam having pressure of more than 0.1 MPa and less than 0.3 MPa and temperature of 200 to 500° C. By adopting the induction heating method mentioned above, it is possible to change the water into superheated steam of more than 200° C. for a short time from the conduction starting time.

In FIG. 4, reference numeral 14 denotes a tubular nozzle. This tubular nozzle 14 is attached to a tip end of a conduit 15 connected to a terminal end of the water-pass pipe of the superheated steam generator 13 so as to be suspended downward, and the tubular nozzle 14 has a tip end opening 14a directed downward.

The preform 1 is conveyed along one direction directly under the circular opening 14a of the tubular nozzle 14 in a vertically elected state with the mouth portion 1a being directed upward. The conveying mode may be a continuously conveying mode in which the preforms are continuously conveyed or may be an intermittently conveying mode in which each of the preforms 1 is temporarily stopped directly under the opening 14a of the tubular nozzle 14. The preform 1 is capable of being conveyed by clamping the support ring 3 thereof with a clamper, not shown.

In FIG. 4, reference numeral 16 denotes a nozzle in form of slit. This slit-shaped nozzle 16 is connected to a tip end of a branch tube 15a branched from the conduit 15 in a manner such that the slit 16a of the nozzle 16 faces a side surface of the preform 1. Preferably, a pair of slit-shaped nozzles 16 are arranged so that the preform 1 is sandwiched from both side portions thereof, and the preform 1 is conveyed while rotating an axis thereof. Although it is possible to convey the preform without being rotated, in such case, it may be required for plural paired slit-shaped nozzles to be arranged.

In the illustration of FIG. 4, although the slit-shaped nozzles are shown, annular-shaped nozzles such as tubular nozzles may be disposed to the side surfaces or bottom surface in an opposing manner.

When the preform 1 is sterilized, the superheated steam S is always supplied to the tubular nozzle 14 and the slit-shaped nozzle 16 from the superheated steam generator 13 so that the superheated steam S is jetted toward the preform 1 from the circular opening 14a of the tubular nozzle 14 and the slit 16a of the slit-shaped nozzle 16. The nozzle diameters, angles, preform axis and the like are preliminarily optionally set so that the jetted superheated steam S contacts the entire inner surface of the preform 1.

According to the operation mentioned above, the superheated steam S blasted from the opening 14a of the tubular nozzle 14 enters inside the preform 1 through the mouth portion 1a thereof and contacts the entire inner surface thereof to thereby sterilize general bacteria, fungus, yeast and the like adhering to the inner surface of the preform 1. Further, since such sterilization can be achieved for a short time by blasting the superheated steam S into the interior of the preform 1, the mouth portion 1a of the preform can be prevented from being excessively heated from the interior side of the preform 1 and can be hence surely prevented from being deformed.

Furthermore, the superheated steam S blasted from the slit 16a of the slit-shaped nozzle 16 contacts the entire outer surface of the preform 1, including the mouth portion 1a, now rotating around the axis thereof, thus heating and sterilizing the outer surface of the preform 1. Accordingly, general bacteria, fungus, yeast and the like adhering to the outer surface of the preform 1 can be sterilized. Further, since such sterilization can be achieved for a short time by blasting the superheated steam S into the interior of the preform 1, the mouth portion 1a of the preform can be prevented from being excessively heated from the interior side of the preform 1 and can be hence surely prevented from being deformed.

Figure 5:
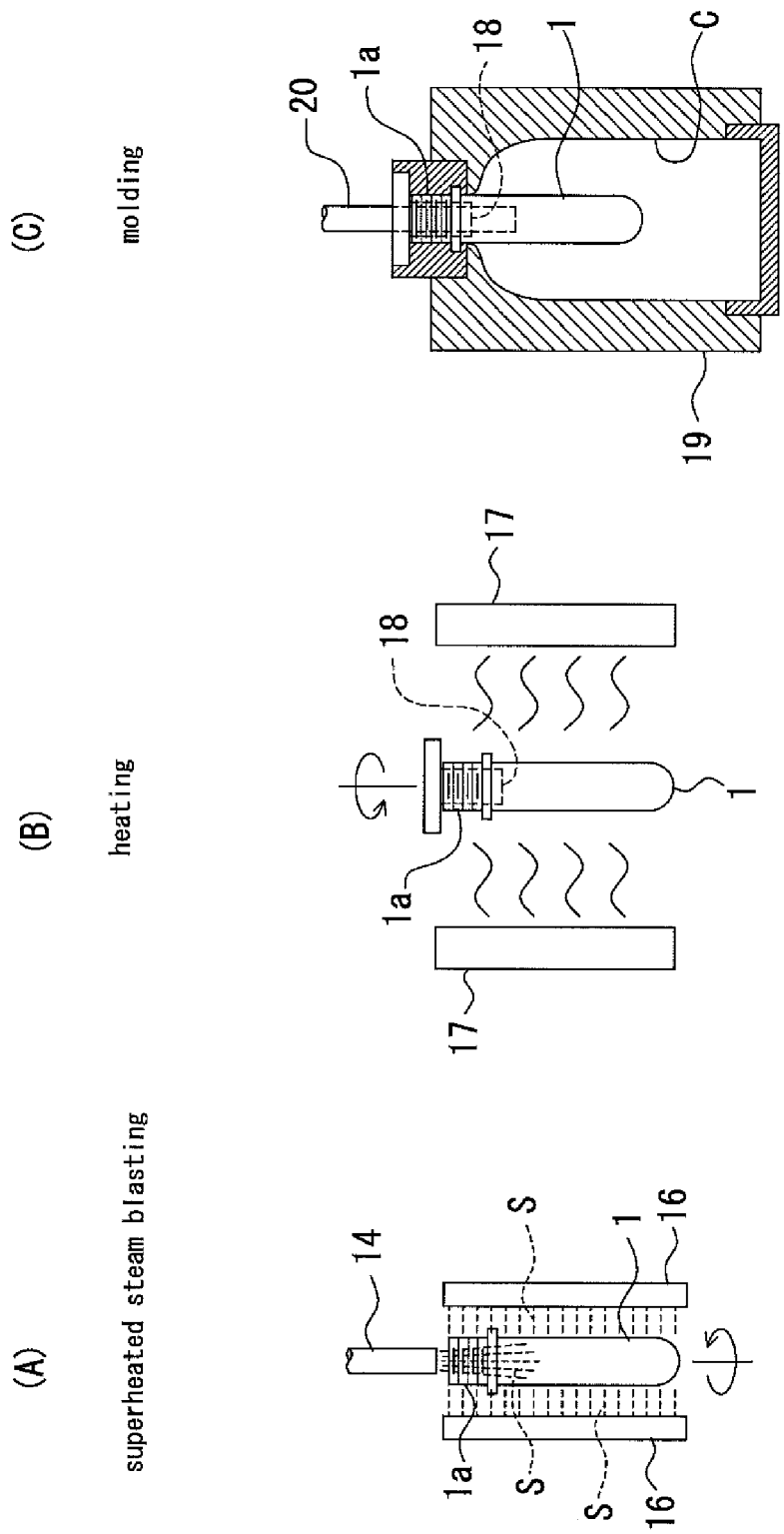
FIG. 5 is an explanation view explaining processes from a process of sterilizing the preform with superheated steam to a process of blow-molding the preform.
Figure 6:
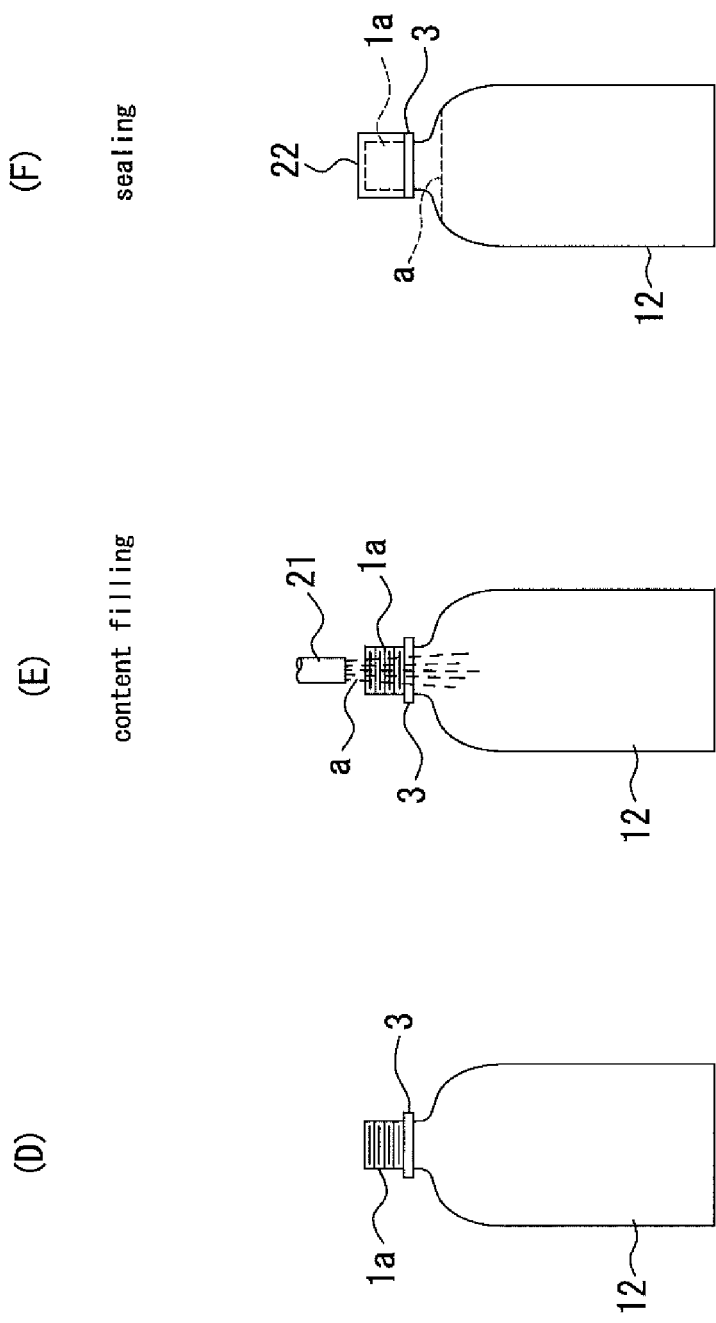
FIG. 6 is an explanatory view showing processes to a capping process after the blow-molding process.
Figure 7:
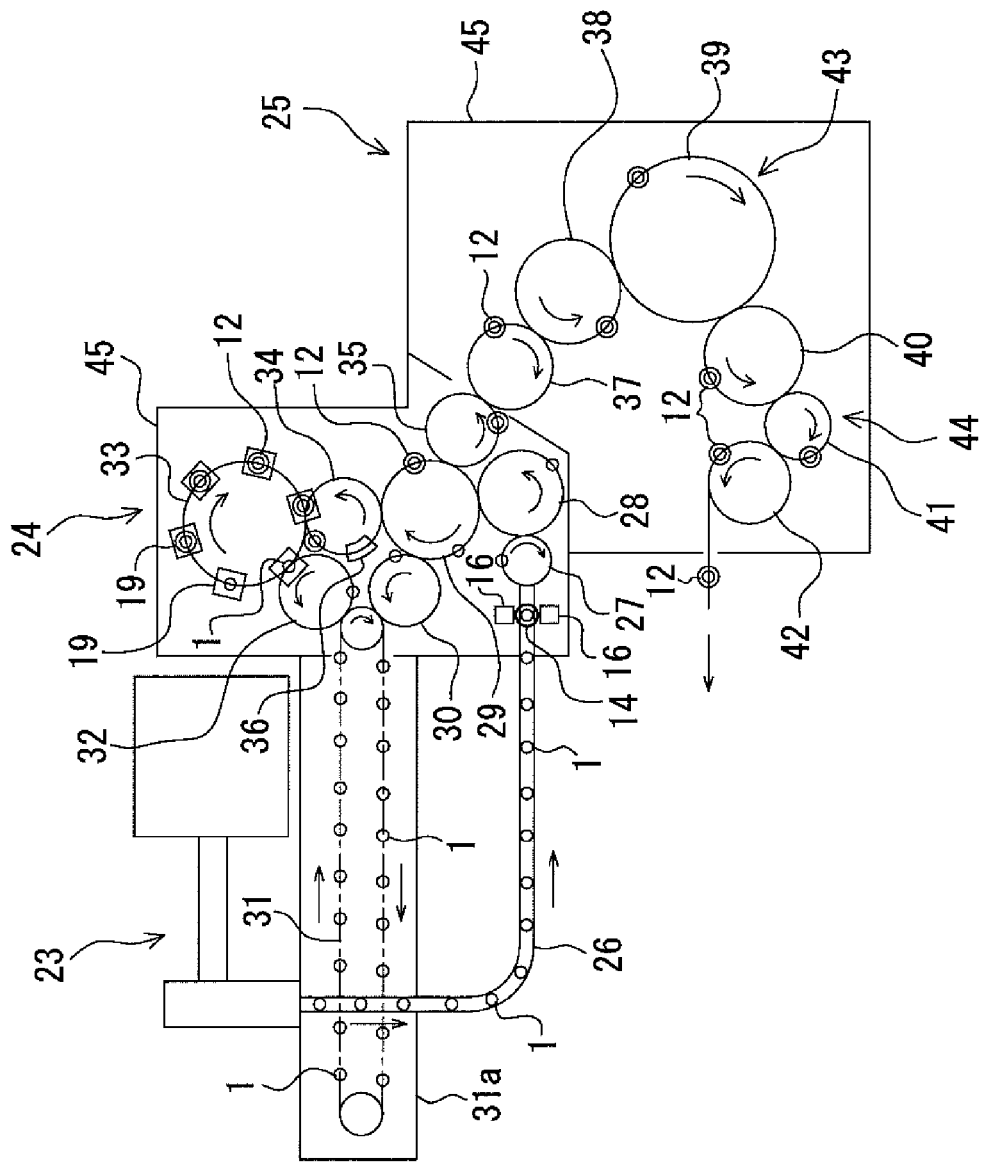
FIG. 7 is a schematic plan view showing a machine for filling the preform with drink after the sterilization with the hydrogen peroxide, the sterilization with superheated steam and the blow molding.

The preform sterilizing means using the superheated steam S is incorporated in an inline system shown in FIGS. 5 to 7 to thereby produce a large amount of aseptic packaging products.

In this inline system, the preforms 1 are continuously delivered at a predetermined speed, and manufactured as aseptic packaging products through processes shown in FIGS. 5 and 6.

First, as shown in FIG. 5(A), the preform 1 passes a position at which the tubular nozzle 14 and the slit-shaped nozzle 16 are disposed at a predetermined travelling speed while travelling with its vertically elected posture being maintained. During this passing, as mentioned above, the superheated steam S is blasted into the interior of the preform 1 through the mouth portion 1a and also blasted to the outer surface thereof, so that the entire surfaces including inner and outer surfaces of the preform 1 can be sterilized for a short time.

In the illustrated example, although the preform 1 is maintained in its vertically elected posture, it may be possible for the preform 1 to have its inverted posture.

Since such sterilization as described above is performed for a short time, the mouth portion 1a of the preform 1 is free from deformation and resin material forming the preform is not excessively heated. In addition, since steam drain is not dewed and remains on the surface of the preform, the bottle 12 molded in the blow-molding process performed thereafter is never whitened.

Further, the inner and outer surfaces of the preform 1 may be sterilized by alternatively shifting the tubular nozzle 14 and the slit-shaped nozzle 16 in arrangement.

As shown in FIG. 5(B), a heater 17 is disposed in a wall-like arrangement along the conveying path of the preform 1, and the preform 1 is heated, while travelling, by the heater 17 uniformly to a temperature of about 90° C. to 130° C. suitable for the subsequent blow-molding treatment.

In the heating period, a spindle 18 is inserted into the preform 1 through the mouth portion 1a thereof to be suspended in the elected state and rotated with the spindle 18 to be thereby uniformly heated by the heater 17.

The preform 1 heated to a temperature suitable for the blow-molding treatment is subjected to the blow-molding treatment as shown in FIG. 5(C), and then formed into the bottle 12 as a container.

A mold 19 as a blow-molding mold is continuously traveled at the same speed as the travelling speed of the preform 1, the preform 1 is clamped, the blow-molding is performed to the preform within the mold 19, and the mold 19 is thereafter opened.

The preform 1 has been heated substantially uniformly so that the entire temperature of the preform increases to a temperature range suitable for the molding treatment in the heating process shown in FIG. 5(B), and with this temperature being maintained, the preform 1 is inserted into the mold 19 together with the spindle 18 as shown in FIG. 5(C). Further, the blow nozzle 20 is inserted into the preform 1 passing the upper portion of the mold 19 and penetrating the spindle 18 in the mouth portion 1a of the preform 1.

While travelling the mold 19, for example, primary air for blowing and secondary air for blowing are blasted into the preform from the blow nozzle 20, and the preform 1 is thereby swelled in the cavity C of the mold 19 into the bottle 12 as final product.

As described above, when the bottle 12 is molded into the mold 19, the mold 19 is opened while travelling, and as shown in FIG. 6(D), the product bottle 12 is taken out of the mold 19.

After the molding treatment, the bottle 12 is continuously traveled, and thereafter, as shown in FIG. 6(E), every kind of drinks a such as mineral water, tea, milk, carbonated drink, or like drink is filled as inner content into the bottle 12 through a filling nozzle 21, and as shown in FIG. 6(F), a cap 22 as a lid is applied to the bottle to seal the bottle 12.

Further, it may be preferred that the sterilizing effect is enhanced by sterilizing the outer surface of the bottle 12 by the spray of a sterilizing agent such as hydrogen peroxide or irradiation of electron ray or like to the bottle 12 after the blow-molding treatment. In a case where the inner surface of the bottle is sterilized by the hydrogen peroxide water mist, it is necessary to passively reduce concentration of the hydrogen peroxide to eliminate possibility of remaining of the hydrogen peroxide inside the bottle.

After the above treatments, the bottles 12 produced as product to be packaged are collected and transported to markets.

An aseptic filling system for effecting the inline system mentioned above has a configuration or structure such as shown in FIG. 7, for example.

As shown in FIG. 7, this aseptic filling system is provided with a preform supplying machine 23 for subsequently supplying bottomed tubular preforms 1 each having a mouth portion 1a (see FIGS. 4, and 5(A)) at a predetermined interval, a blow-molding machine 24 and a filling machine for filling the molded bottles 12 with the drink a and then sealing the bottles 12.

The preform supplying machine 23 is configured to take out the preforms 1 one by one from a packaged large-sized container in which the preforms 1 are accommodated, and the preforms 1 are transported to the first conveying path described hereinafter. In the case where the conveyer 4 mentioned above is arranged within the same factory in which the aseptic filling system is installed, it may be possible to directly connect the conveyer 4 to the preform supplying machine 23.

On a root from the preform supplying machine 23 to the filling machine 25, there are provided a preform conveying means for conveying the preforms 1 on the first conveying path, a mold conveying means for conveying the mold 19 (see FIG. 5(C)) having the cavity C of the shape corresponding to the product of the bottle 12 on the second conveying path connected to the first conveying path, and a bottle conveying means for conveying the bottles 12 molded by the mold 19 on the third conveying path connected to the second conveying path.

The first conveying path of the preform conveying means, the second conveying path of the mold conveying means and the third conveying path of the bottle conveying means are communicated with each other, and grippers and like members, not shown, for holding and conveying the preforms 1 and the bottles 12 are provided on these conveying paths.

The preform conveying means is provided, on its first conveying path, with a preform conveyer 26 for subsequently conveying the preforms 1 at a predetermined interval. The preform conveying means is further provided with a train of wheels 27, 28, 29 and 30 which receive the preforms 1 from the terminal end of the conveyer 26 and a conveyer 31 which receives the preforms 1 from the wheel 30 and then conveys the preforms 1.

The tubular nozzle 14 and the slit-shaped nozzle 16 for blasting the superheated steam S to the preform 1 are provided on the slightly upstream side of a portion of the preform supplying machine 23 at which the preform conveyer 26 is connected to the wheel 27. The superheated steam S is blasted toward the preforms 1 before heating (see FIGS. 4 and 5(A)) from these nozzles 14 and 16, thereby uniformly heating and sterilizing the inner and outer surfaces of the preform 1.

These nozzles 14 and 16 may be provided on predetermined positions on the outer periphery of the wheel, for example, before the preform 1 reaches the conveyer 31.

The conveyer 31 includes an endless conveying chain extending longwise in the horizontal direction, and a heating unit 31a is disposed along the endless conveying chain. A number of spindles 18, one shown in FIG. 5(B), are mounted to the endless conveying chain at a constant pitch between adjacent ones. Each spindle 18 can rotate while travelling with the running of the endless conveying chain. As shown in FIG. 5(B), the spindle 18 is inserted into the preform 1, through the mouth portion 1a thereof, conveyed to the conveyer 31 from the wheel 30, and the preform 1 is held in its elected posture by the spindle 18.

The preform 1 is received by the conveyer 31 through the preform conveyer 26 and the train of the wheels 27, 28, 29, 30 and reciprocates within the heating unit 31a by the conveyer 31. The heaters 17 are attached in a spread manner on the inner wall sections of the heating unit 31a (see FIG. 5(B)), and the preform 1 is heated by the heaters while being conveyed by the conveyer 31. The preform 1 rotates together with the rotation of the spindle 18 during the travelling on the conveyer 31 and is uniformly heated by the heaters 17.

The blow-molding machine 24 is provided with plural sets of the molds 19 and blow nozzles 20 (see FIG. 5(C)) receiving the preform 1 heated in the heating unit 31a of the preform supplying machine 23 and then heating and molding the preform 1 into the bottle 12.

The second conveying path of the mold conveying means described hereinbefore is arranged within the blow-molding machine. This second conveying path includes a train of wheels 32, 33, 34, 29 and 35. It is further to be noted that the wheel 29 is commonly used in the train of wheels 32, 33, 34, 29, 35 and the train of wheels 27, 28, 29, 30.

A plurality of such molds 19 and blow nozzles 20 are arranged around the wheel 33 and turned at a constant speed around the wheel 33 together with the rotation of the wheel 33.

When the preform 1 heated in the heating unit 31a of the preform supplying machine 23 is received by the gripper, not shown, together with the spindle 18, and is transferred to the mold 19 disposed around the wheel 33, the mold 19 now split in opened state is closed to thereby holds the preform 1 as shown in FIG. 5(C). The preform 1 inside the mold 19 are turned around the wheel 33 together with the mold 19 and the blow nozzle 20. During such operation, the preform is subjected to the blow-molding treatment with highly pressurized air blown from the blow nozzle 20, thereby being formed into a product bottle 12. As shown in FIG. 5(B), since the preform 1 is uniformly heated to the predetermined temperature by the heater 17, the blow-molding treatment can be smoothly performed.

When the preform 1 disposed inside the cavity C of the mold 19 tightly contact the inner surface of the mold 19 and the bottle 12 is formed, the mold 19 is opened at a time when the mold 19 contacts the wheel 34, and the bottle 12 and the spindle 18 are then released. Then, the bottle 12 is transferred to the gripper, not shown, of the wheel 34 from the spindle 18.

On the other hand, the spindle 18 after releasing the bottle 12 is returned to the conveyer 31 through the wheel 32 and takes a position ready for holding and conveying another preform 1.

The bottle 12 released from the blow-molding machine 24 and reaches the wheel 34 is subjected to the inspection whether the bottle is right or wrong as a molded product (i.e., defective or not in molding treatment) by an inspection device 36 provided at the outer peripheral portion of the wheel 34.

The inspection device 36 is provided, not shown, with a bottle body inspection means for discriminating whether the bottle body is right or wrong, a support ring inspection means for discriminating whether the support ring 3 (FIG. 1) of the bottle 12 is right or wrong, a bottle neck ceiling inspection means for discriminating whether the neck ceiling portion of the bottle 12 is right or wrong, and a bottle bottom inspection means for discriminating whether the bottle bottom portion is right or wrong.

The bottle body inspection means, the support ring inspection means, and the bottle neck ceiling inspection means are arranged along the outer periphery of the wheel 34.

The bottle body inspection means, the support ring inspection means, and the bottle neck ceiling inspection means are provided with lamps and cameras for photographing predetermined portions of the bottle 12, and image processing units for processing the photographed images to thereby discriminate the abnormality of the bottle with respect to the shape, injury, foreign material, color and the like thereof.

Further, the inspection device 36 is disposed optionally as occasion demands, and the bottle body inspection means, the support ring inspection means and the bottle neck ceiling inspection means may be selectively arranged as occasion demands.

The bottle 12, which is judged as defective product after the inspection, is rejected from the conveying path by a rejecting device, not shown, and only acceptable product is conveyed to the wheel 35 from the wheel 34 through the wheel 29.

Further, it may be possible to additionally sterilize the outer surface of the bottle 12 after the blow-molding treatment by spray of steam including a sterilizing agent such as hydrogen peroxide or irradiation of electron ray, or possible to enhance the sterilizing effect for the inner surface of the bottle. For example, sterilization means such as sterilizing agent including steam spray device or electron ray irradiation device may be provided for the wheel 29 or 35.

The filling machine 25 is provided therein with the third conveying path of the bottle conveying means. This third conveying path includes a train of wheels 37, 38, 39, 40, 41 and 42.

A filler 43 for filling the bottle 12 with the drink a and a capper 44 for applying a cap 22 (see FIG. 6(F)) to the bottle 2 to seal the same are disposed within the filling machine 25.

It is further to be noted that since known filler and capper are usable as such filler 43 and capper 22, the explanation thereof will be omitted herein.

The filling system is surrounded by a chamber member 45 (called merely chamber hereinafter), and the interior of the chamber 45 is sectioned into an aseptic zone and gray zone. The preform supplying machine 23 and the blow-molding machine 24 are disposed in the gray zone, and the filling machine 25 is disposed in the aseptic zone, respectively.

Aseptic air sterilized in the HEPA is always blown into the gray zone, thereby conveying the bottle sterilized in the molding process to the aseptic zone without being secondarily contaminated by bacteria or like.

Further, in a case where a portion of the conveyer 4 that is downstream side of the chamber 45 is connected to the preform supplying machine 23, the preform 1 sterilized by the hydrogen peroxide is further sterilized by the superheated steam S and is then subjected to the blow-molding treatment to be thereby molded into a container such as bottle. Furthermore, in a case where the blow-molding machine 24 is connected to the drink filling machine 25, the bottle 12 is filled up with the drink a, sealed and discharged as an aseptically filling packaged product.

Next, the function and operation of the preform sterilizing system shown in FIGS. 2 and 3 and the aseptic filling system shown in FIG. 7 will be explained together with the preform sterilizing method.

Beforehand the sterilization treatment of the preform 1, the hydrogen peroxide water is preliminarily sprayed into the chamber 5 through the spray nozzle 10 and the interior of the chamber 5 is thus sterilized Moreover, the interior of the chamber 37 of the aseptic filling system 37 is likewise sterilized.

By driving the preform molding machine, the molded preform 1 is loaded on the upstream side of the conveyer 4 now travelling. The preform 1 discharged from the preform molding machine is received on the upstream side portion of the conveyer 4, and as shown in FIG. 2, the preforms 1 are scraggly overturned on the conveyer 4.

The preform 1 on the conveyor 4 enters the chamber 5 together with the conveyor 4 and is sprayed with the hydrogen peroxide water by the spray nozzle 10.

The mist of the hydrogen peroxide water is discharged in a direction crossing the conveyor 4 from both sides thereof, and the preform 1 is overturned on the conveyor 4 by vibration or like, so that the hydrogen peroxide can uniformly adheres to the outer surface of the preform 1.

The hydrogen peroxide water mist flows into the preform 1 in the overturned state through the mouth portion 1a thereof to thereby uniformly adhere to the inner surface of the preform 1.

The hydrogen peroxide water mist discharged from the spray nozzle 10 fills the interior of the chamber 5 and circulates therein, so that the hydrogen peroxide water mist adheres uniformly to the inner surface of the preform 1 while flowing therein. Thus, the entire surface of the preform 1 can be uniformly sterilized by the hydrogen peroxide.

The preform 1 passes through the chamber 5 together with the conveyor 4 while being blasted with the hydrogen peroxide water mist, and is then charged into a container such as large luggage container.

This large container is transported to a factory in which the aseptic filling system is installed, and the container is opened there and the preforms 1 in the large container are transferred to the preform supplying machine 23.

Then, the preforms 1 are transferred to the conveyor 26 in an aligned state by the preform supplying machine 23 and then transferred to the heating unit 31a by means of the train of the wheels 27, 28, 29 and 30.

Before the preform 1 enters the heating unit 31a, the superheated steam S is blasted toward the inner and outer surfaces of the preform 1 from the nozzles 14 and 16 shown in FIG. 4 (see FIG. 5(A)), thereby sterilizing the entire surface of the preform 1.

In the heating unit 31a, the preform 1 is entirely uniformly heated to a temperature of a range suitable for the following molding treatment while being conveyed by the conveyor 31 (see FIG. 5(B)).

The preform 1 heated in the heating unit 31a is held by the mold 19 during the passing around the outer periphery of the wheel 33, and the preform 1 trapped inside the mold 19 is swelled into a bottle as a product in the cavity C by blasting the highly pressurized air from the blow nozzle 20 (see FIG. 5(C)).

The molded bottle 12 (see FIG. 6(D)) is taken out of the mold 19 by the gripper of the wheel 34 after opening the same, and thereafter, is inspected by the inspection device 35 to confirm whether the molding treatment is preferably performed or not.

Thereafter, the bottles 12 travel inside the filling machine 25 while being transferred to the train of the wheels 38, 39, 40, 41 and 42.

Within the filling machine 25, the bottle 12 is filled up with the drink a that has been subjected to the sterilizing treatment as shown in FIG. 6(E) by the filler nozzle 21 of the filler 43. The sterilized cap 22 is then applied to the mouth portion 1a of the bottle 12 by the capper 44, and the bottle 12 is then sealed (see FIG. 6(F)) and discharged out of the chamber 45.

As described hereinbefore, since the filler 43 and the capper 44 are known ones, the explanation of the drink filling method for the bottle and the bottle sealing method will be omitted herein.

Example 2

Mist of hydrogen peroxide water was produced by supplying hydrogen peroxide water of 35% concentration and pressurized air to a two-fluid spray, the thus produced mist was mixed with hot air having temperature of 60° C., and then, the mist of the hydrogen peroxide water was sprayed inside a chamber through a nozzle. The chamber has a size of 600 mm width, and a conveyor has 1.5 m length. Preforms, each being formed into a bottle of 500 mm, were supplied to the conveyor by the number of 860 bottles/min., and the conveyor was driven at a speed of 0.2/sec. At this time, the hydrogen peroxide water of amount of about 50 mg adhered to each preform. Furthermore, preforms, each being formed into a bottle of 2000 mm, were supplied by the number of 250 bottles/min., and the same operation was performed. At this time, the hydrogen peroxide water of amount of about 150 mg adhered to each preform. Such preforms were subjected to the following treatment.

Superheated steam of flow amount of 0.7 g/sec. generated by heating water by a superheated steam generator of induction heating system was sprayed to each inner surface of the preform from a nozzle having inner diameter of 8 mm at blasting temperature of 300° C. for 5 sec.

In such spraying, the sterilizing effect is shown in Table 1 in an evaluation with indicating *bacillus* inoculated on the inner surface of the initial preform, and it was confirmed that this sterilizing effect is applicable to every drink.

TABLE 1

|  | B. sub. | A. nig |
| --- | --- | --- |
| For 500 mL | 3.1D | More than 6.0D |
| For 2 L | 3.0D | More than 6.0D |

In the above Table 1, term "B.sub." is an abbreviated term of "*BaciLLus subtiLis*", and "A.nig." is an abbreviated term of "*AspergiLLus niger*". "D" is a D-valve indicating the sterilizing effect.

Further, an experiment result of deformed amount of the inner diameter of the mouth portion of the preform indicated no problem for maintaining the sealing performance of a cap as shown in the following Table 2.

TABLE 2

|  | Before Blasting Of Superheated Steam | After Blasting Of Superheated Steam |
| --- | --- | --- |
| For 500 mL | 21.77 mm | 21.75 mm |
| For 2 L | 21.75 mm | 21.71 mm |

Example 3

The hydrogen peroxide water adhered to each preform having inner volume of 500 ml for bottle as in the first example 1. Furthermore, superheated steam of flow amount of 0.7 g/sec. generated by heating water by a superheated steam generator of an induction heating system was sprayed to the inner surface of each preform from a nozzle having inner diameter of 8 mm at blasting temperature in a range of 180 to 550° C. for 10 to 3 sec.

The sterilizing effect and the deformation of the inner diameter of the preform by such superheated steam spraying is shown in the following Table 3.

TABLE 3

| Blasting Temperature (° C.) | Blasting Time (sec.) | Sterilizing Effect | Deformation |
| --- | --- | --- | --- |
| 180 | 10 | X | X |
| 250 | 6 | ○ | ○ |
| 350 | 4 | ○ | ○ |
| 450 | 3 | ○ | ○ |
| 550 | 3 | ○ | X |

Further, it is to be noted that, in the above Table 3, the sterilization effect is shown with [○] (good) in the case where the D-value with respect to *BaciLLus subtiLis* is not less than 6, and the other cases are shown with [x] (not good). With respect to the deformation of the inner diameter, in the case where the inner diameter of the preform is deformed by less than 0.05 mm is shown with [○] (good), and the other cases are shown with [x] (not good).

Embodiment 3

Hereunder, the third embodiment 3 of the present invention will be explained.

Preforms as targets in the present embodiment are the same as those in the first embodiment 1.

Figure 8:
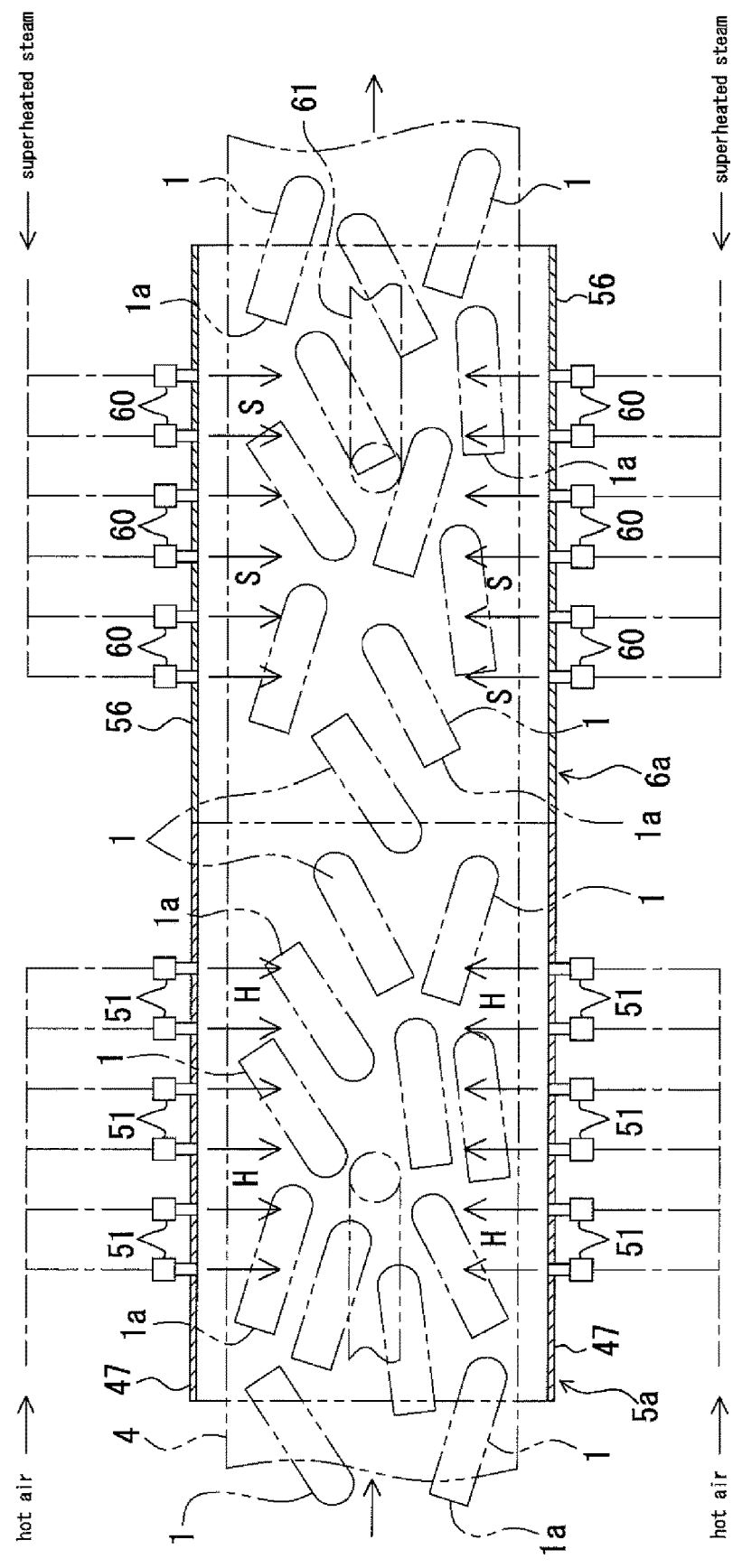
FIG. 8 is a partially cut-off plan view showing a schematic structure of an apparatus for carrying out a method of sterilizing a preform according to the present invention.
Figure 9:
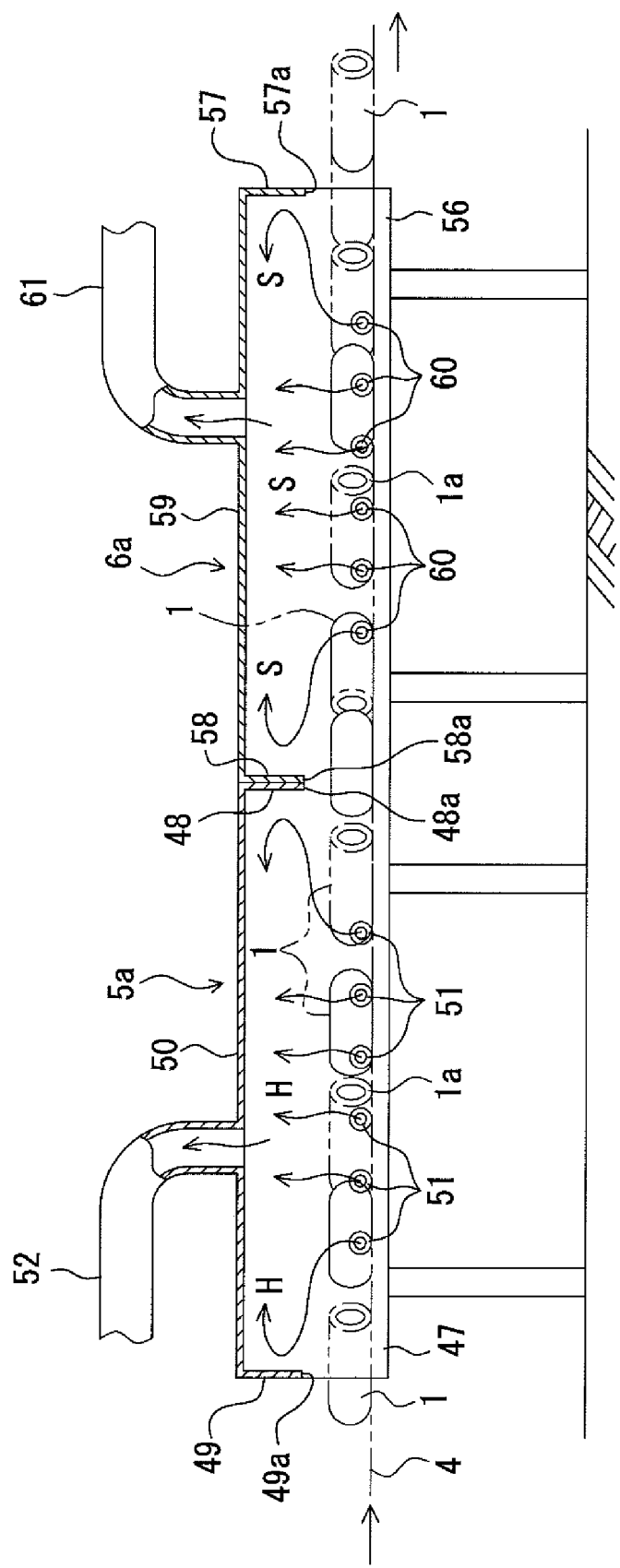
FIG. 9 is a vertical sectional view showing a schematic structure of the apparatus mentioned above.

A device for sterilizing the preform 1 has a structure or configuration shown in FIGS. 8 and 9.

In FIGS. 8 and 9, reference numeral 4 denotes an endless belt-type conveyer. A preform molding machine, not shown, is disposed on the upstream side in the travelling direction of the conveyer as indicated with an arrow. The preform 1 after being molded and released from the preform molding machine is received by using a hopper or like, not shown, on the upstream side of the conveyer 4. As shown in FIG. 8, the molded preforms 1 are laid in the scraggly overturned manner on the conveyer 4.

An intermediate portion of the conveyer 4 can be traveled in the horizontal direction, and in this intermediate portion, the first and second chambers 5a and 6a are arranged in an aligned manner and are applied to the conveyer 4 each in form of hood.

As shown in FIGS. 8 and 9, the first chamber 5a is defined by both side wall sections 47 disposed so as to sandwich the conveyer 4 from both sides, front and rear wall sections 48 and 49 disposed at front and rear ends of both the side wall sections 47, and a top wall section 50 shielding the upper side of both the side wall sections 47 and the front and rear wall sections 48 and 49.

A preheating nozzle (nozzle for preheating) 51 exhausting hot air H in a direction crossing the conveyer 4 from the side edge side of the conveyer is mounted to each of both the side wall sections 47. Although it may be possible to mount one preheating nozzle 51 to each side wall section 47, it is preferred to arrange a plurality of preheating nozzles 51 to each side wall section along the travelling direction of the conveyer 4.

Further, the preheating nozzle 51 having a circular opening or a slit-shaped opening may be preferably used.

The aseptic hot air H is supplied from the upstream side of each preheating nozzle 51, and the hot air H is discharged into the first chamber 5a through the tip ends of the respective preheating nozzles 51 and blasted to the surface of the preform 1 on the conveyer 4 to thereby preheat the surface of the preform 1 by the heat of the hot air H.

It is preferred that the temperature of the hot air H discharged from the preheating nozzle 51 is 80 to 130° C., and the surface temperature of the preform 1 preheated by the hot air H is preferably of 40 to 70° C. In a case of less than 40° C., the temperature of the superheated steam S or like basted in the subsequent stage is not so lowered, and in a case of more than 70° C., the mouth portion 1a of the preform 1 may be deformed.

Within the first chamber 5a, the hot air H is discharged in a direction crossing the conveyer from both sides of the conveyer 4, and since the preform 1 can be horizontally overturned on the conveyer 4 by vibration or like, the hot air can uniformly contact the surface of the preform 1. At the same time, since the hot air flows inside the preform 1 through the mouth portion 1a of the overturned preform 1, thereby also uniformly contacting the inner surface of the preform 1. Furthermore, the hot air H discharged from the preheating nozzle 51 fills the interior of the chamber 5a and circulates therein, so that this flow of the hot air H uniformly adheres to the surface of the preform 1. Thus, the entire surface of the preform 1 can be suitably preheated by the hot air H.

The front and rear wall sections 48 and 49 of the first chamber 5a are formed with openings 48a and 49a through which the conveyer 4 and the preform 1 placed thereon can pass. In addition, an exhaust duct 52 is connected to the top wall section 50 of the first chamber 5a. The hot air H discharged into the first chamber 5a is sucked into the exhaust duct 52 by driving a blower, not shown, and then discharged outside the first chamber 5a.

A hot air (H) generation section is provided, as shown in FIG. 10(A), with a blower 53, a sterilizing filter 54 and an electric heater 55. Outdoor air taken by the blower 53 is sterilized by the sterilizing filter 54, then heated by the electric heater 55 to a predetermined temperature, and thereafter, is fed to the respective preheating nozzles 51 through pipes or like as aseptic hot air H.

Further, it may be possible to add heated steam to air flowing toward the sterilizing filter 54 from the blower 53. According to such addition of the heated steam, the air is preheated and humidified, thereby enhancing heat capacity of the aseptic hot air H from the electric heater 55. Moreover, the sterilizing filter 54 may be constituted with a prefilter and an ULPA filter which are connected in series. The provision of the prefilter elongates duration of life of the ULPA filter.

As shown in FIGS. 8 and 9, a second chamber 6a is disposed adjacent to the first chamber 5a on the downstream side of the conveyer 4.

The second chamber 6a is also defined, as like as the first chamber 5a, by both side wall sections 56 disposed so as to sandwich the conveyer 4 from both sides, front and rear wall sections 57 and 58 disposed at front and rear ends of the both side wall sections 56 and 49, and a top wall section 50 shielding the upper side of both the side wall sections 56 and the front and rear wall sections 48 and 49.

A sterilization nozzle (nozzle for sterilization) 60 exhausting superheated steam S in a direction crossing the conveyer 4 from the side edge side of the conveyer 4 is mounted to each of both the side wall sections 56. Although it may be possible to mount one sterilization nozzle 60 to each side wall section 56, it is preferred to arrange a plurality of sterilization nozzles 60 51 to each side wall section 56 along the travelling direction of the conveyer 4.

Further, the sterilization nozzle 60 having circular opening or slit-shaped opening may be preferably used.

The superheated steam S is supplied from the upstream side of each sterilization nozzle 60, and the superheated steam S is discharged into the second chamber 6a through the tip ends of the respective sterilization nozzles 60.

The superheated steam S is a mixed gas of water and hydrogen peroxide made from water mixed with hydrogen peroxide. When this superheated steam S is blasted to the surface of the preform 1 on the conveyer 4, the surface of the preheated preform 1 is sterilized by the combined effects due to the heat of the superheated steam S and the sterilizing function of the hydrogen peroxide.

A temperature for blasting the superheated steam S to the preform 1 is preferably of 150 to 500° C., and more preferably, 250 to 400° C. Within the temperature range of 150 to 500° C., only the surface of the preform is exposed to high temperature, and thereby, fungus or like adhering to the surface of the preform 1 can be sterilized for a short time. In the case of the temperature of less than 150° C., long time blasting of the superheated steam S is required for the sterilization, which will result in temperature increasing of the PET itself constituting the preform 1, hence leading to deformation of the preform. In the case of more than 500° C., the temperature of the PET will be increased for a short time, which will lead to easy deformation of the preform 1.

A pressure of the superheated steam S to be blasted to the preform 1 is higher than atmospheric pressure, and is preferably more than 0.1 MPa and less than 0.3 MPa. In a case where this pressure is near 0.1 MPa, even if the superheated steam S contacts the preform and the temperature thereof is lowered, there is less possibility of condensation (bedewing), and in a case where this pressure is more than 0.3 MPa, when the superheated steam S is blasted to the preform 1, the condensation thereof may be formed on the surface of the preform 1. When such condensation is formed, there may cause a fear of generating whitening to the surface of the bottle 2 at the time of blow-molding the preform into a bottle or like.

Furthermore, it is preferred that the time for blasting the superheated steam S to the preform 1 is within 1.0 to 10.0 sec. In the case of less than 1.0 sec., defective sterilization may be likely caused, and in the case of more than 10.0 sec., the mouth portion 1a of the preform 1 may be likely deformed. This superheated steam blasting time can increase the sterilizing effect by the superheated steam S consisting of water mixed with the hydrogen peroxide because the surface of the preform 1 is preliminarily heated as mentioned hereinbefore in comparison with a case in which the preheating is not effected.

It is preferred that the hydrogen peroxide to be mixed with the water has concentration of 0.5 to 15%. In the case of less than 0.5%, the sterilizing power against the spore-forming bacteria is insufficient, and in the case of more than 15%, the hydrogen peroxide will remain much.

The superheated steam S is discharged in a direction crossing the conveyer 4 from both sides of the conveyer 4 within the second chamber 6a, and since the preform 1 is overturned on the conveyer 4 by vibration or like, the superheated steam S is uniformly contacts or adheres to the surface of the preform 1. Moreover, since the superheated steam S discharged from the sterilization nozzle 20 fills and circulates in the second chamber 6a, this superheated steam S also uniformly contacts or adheres to the surface of the preform 1. Thus, the entire surface of the preform 1 is properly sterilized by the superheated steam S and the hydrogen peroxide contained therein.

The front and rear wall sections 57 and 58 of the second chamber 6a are formed with the openings 57a and 58a so that the conveyer 4 and the preforms 1 placed thereon can pass through the openings. An exhaust duct 61 is connected to the top wall section 59 of the second chamber 6a. The superheated steam S discharged into the second chamber 6a is sucked into the exhaust duct 61 by the operation of the blower, not shown, and then discharged outside the second chamber 6a.

The superheated steam S can be obtained by using a commercially sold superheated steam generator 62 shown in FIG. 10(B). More specifically, the superheated steam generator of UPSS (Trade Name of TOKUDEN Kabushiki Kaisha). This generator is composed of such a structure as that an induction heating coil is inserted into a central portion of spiral of a water-pass pipe formed from spirally wound-up conductive body, not shown, in which water mixed with the hydrogen peroxide is guided into the water-pass pipe and A.C. voltage is applied to the induction heating coil to thereby generate superheated steam. Current conduction may be possible by frequency-converting the A.C. voltage by an inverter. By the application of the A.C. voltage, the induction heating coil generate the A.C. flux, an induction current passes in the water-pass pipe, and the water-pass pipe is thereby heated. According to this heat generation of the water-pass pipe, the water flowing the water-pass pipe and the hydrogen peroxide are heated and changes to a saturated steam, which is then converted into the superheated steam S, which is then taken out of the water-pass pipe.

Further, by forming the induction heating coil as a conductive tube, the heating effect to the water passing through this water-pass pipe may be enhanced.

According to the superheated steam generator 62 of the structure mentioned above, it is possible to obtain a superheated steam as the superheated steam S having a pressure of 0.1 MPa and a temperature of 150 to 500° C. By adopting the induction heating method mentioned above, the water mixed with the hydrogen peroxide is changed into the superheated steam S having the temperature of 150 to 500° C. for a short time from the conduction-start time. More specifically, the superheated steam S is a high-temperature mixed gas of the water and the hydrogen peroxide, and this superheated steam S is taken out from the tip end of the conduit 63 connected to the terminal end of the water-pass pipe of the superheated steam generator 22 and then distributed to the respective sterilization nozzles 60.

The downstream side furtherer than the second chamber 6a of the conveyer 4 extends toward a large container, not shown. The preform 1 sterilized within the second chamber 6a by the superheated steam S is delivered toward and then into the large container by the conveyer 4. This large container is sealed after the accommodation of predetermined amount of the preforms and stored, and then transferred to a factory in which the preforms are molded into bottles.

Further, in an arrangement in which the downstream side furtherer than the second chamber 6a of the conveyer 4 is connected to the blow-molding machine, the sterilized preform 1 is immediately blow-molded into a container such as bottle. Moreover, in an arrangement in which the blow-molding machine is connected to the content filling machine, the container such as bottle is filled with a content such as drink, sealed and then discharged as the aseptic package of products.

Hereunder, function of the preform sterilization apparatus of the structure mentioned above will be described together with a preform sterilizing method.

Beforehand the starting of the sterilizing treatment of the preform 1, the interiors of the first and second chambers 5a and 6a are preliminarily sterilized by spraying chemical agent such as hydrogen peroxide water or like.

The molded preforms 1 are loaded on the upstream side portion of the travelling conveyer 4 by driving the preform molding machine. The preforms 1 discharged from the preform molding machine is received at the upstream side portion of the conveyer 4 in the overturned manner on the conveyer 4 as shown in FIGS. 8 and 9.

The preform 1 on the conveyer 4 is moved into the first chamber 5a with the conveyer 4, and is then preheated therein by blasting the hot air H discharged from the preheating nozzle 51.

The hot air H is discharged within the first chamber 5a in a direction crossing the conveyer 4 from both sides thereof, and the preform 1 is overturned on the conveyer 4 by vibration or like, so that the hot air H can uniformly contact the outer surface of the preform 1.

The hot air H flows into the preform 1 in the horizontally overturned state through the mouth portion 1a thereof to thereby uniformly adhere to the inner surface of the preform 1.

The hot air H discharged from the preheating nozzle 51 fills the interior of the chamber 5a and circulates therein, so that the hot air H adheres uniformly to the inner surface of the preform 1 while flowing therein. Thus, the entire surface of the preform 1 can be uniformly sterilized by the hot air H.

The preform 1 passes through the chamber 5 together with the conveyer 4 while being blasted with the hot air H, and then enters the second chamber 6a in which the preform 1 is sterilized by blasting the superheated steam S discharged from the sterilization nozzle 60.

According to the above sterilizing treatment, general bacteria, fungus, yeast and the like adhering to the surfaces of the preform 1 can be sterilized by the heat of the superheated steam S and the hydrogen peroxide, and the spore-forming bacteria adhering to the surface of the preform 1 can be also sterilized by the hydrogen peroxide.

The preforms 1 subjected to the sterilizing treatment discharged from the second chamber 6a together with the travelling of the conveyer 4 are then transferred into the large container, or transferred to the blow-molding machine and filling machine without being packaged in the container and then discharged as aseptic packaged products.

It is further to be noted that the present invention is not limited to the above-described embodiment and many other modification may be embodied.

Example 4

The first chamber 5a and the second chamber 6a have size of 1000 mm width, and 1500 mm length, and 200 mm height, respectively. Preforms, each being formed into a bottle of 500 ml, were supplied to the conveyer by the number of 860 bottles/min., and the conveyer was driven at a predetermined speed. In this operation, the temperature of the hot air H in the first chamber 5a, and the blasting temperature of the superheated steam S in the second chamber 6a, and the concentration of the hydrogen peroxide were set as shown in the Table 4, which also shows obtained sterilization results.

TABLE 4

| Hydrogen Peroxide Concentration (%) | Hot Air Temperature In First Chamber (° C.) | Superheated Steam Blasting Temperature In Second Chamber (° C.) | Travelling Speed (m/sec.) | B. sub. | A. niger |
|---|---|---|---|---|---|
| 3 | 100 | 200 | 0.2 | 5.3D | More Than 6.0D |
| 3 | 100 | 400 | 0.2 | 6.0D | More Than 6.0D |
| 3 | NO | 400 | 0.2 | 4.0D | 6.0D |
| 3 | 100 | 500 | 0.2 | More Than 6.0D | More Than 6.0D |
| 10 | 100 | 400 | 0.5 | More Than 6.0D | More Than 6.0D |
| 10 | NO | 400 | 0.5 | 5.5D | More Than 6.0D |
| 10 | 80 | 400 | 0.2 | 6.0D | More Than 6.0D |

The superheated steam S is blasted to the preform 1 as a high temperature mixture gas of the water and the hydrogen peroxide.

The superheated steam S is discharged within the second chamber 6a in a direction crossing the conveyer 4 from both sides thereof, and the preform 1 is overturned on the conveyer 4 by vibration or like, so that the superheated steam S can uniformly contact or adhere to the outer surface of the preform 1.

The superheated steam S flows into the preform 1 in the horizontally overturned state through the mouth portion 1a thereof to thereby uniformly contact or adhere to the inner surface of the preform 1, thus the preform 1 being sterilized.

The superheated steam S discharged from the sterilization nozzle 60 fills the interior of the chamber 6a and circulates therein, so that the superheated steam S uniformly contacts or adheres to the inner surface of the preform 1 while flowing therein.

In the above Table 4, term "B.sub." is an abbreviated term of "BaciLLus subtiLis", and "A.nig." is an abbreviated term of "AspergiLLus niger". "D" is a D-valve indicating the sterilization effect.

As is apparent from the above Table 4, in the case where the superheated steam S added with the hydrogen peroxide was blasted with respect to the A. niger, the sterilizing effect more than 6.0 D could be obtained regardless of the preheating to the surface of the preform by the hot air. With respect to the B.sub, in the case where the preheating was performed and the superheated steam added with the hydrogen peroxide was blasted, the sterilizing effect more than 6.0 D could be obtained, in comparison with the case of no preheat treatment, without increasing the superheated steam temperature or increasing the blasting amount thereof.

Embodiment 4

Hereunder, an embodiment 4 of the present invention will be described, and a preform as a target to be sterilized by the present invention is the same as that in the embodiment 1.

An apparatus for sterilizing the preform 1 has the same structure as that of the embodiment 3 shown in FIGS. 8 and 9.

In this embodiment 4, different from the embodiment 3, the superheated steam S not including hydrogen peroxide is supplied from the upstream side of the respective sterilization nozzles 60, and this superheated steam S is discharged into the second chamber 6a from the tip ends of the respective sterilization nozzles 60 and then blasted to the surfaces of the preforms on the conveyor 4. The surfaces of the preforms 1 that are preheated in the first chamber 5a are thus sterilized by the heat of the superheated steam S.

The temperature of the superheated steam S to be blasted to the preform 1 is preferably of 200 to 700° C., and more preferably, 250 to 500° C. In the case of the temperature range within 200 to 700° C., only the surface of the preform is exposed to highly heated temperature to thereby spore-forming bacteria adhering to the surface of the preform can be sterilized for a short time. In the case of less than 200° C., it is required for the preform to be blasted with the superheated steam for a long time for the sterilization, which leads to highly increased temperature of a PET forming the preform and the preform is hence liable to be deformed. On the other hand, in the case of more than 700° C., the PET forming the preform is itself highly heated for a short time, and is hence liable to be easily deformed.

The pressure of the superheated steam to be blasted to the preform is one higher than atmospheric pressure and is preferably of higher than 0.1 MPa and less than 0.3 MPa. In the case of near 0.1 MPa, even if the temperature is lowered in contact of the superheated steam S to the preform, there is less possibility of condensation of the steam, but in the case of more than 0.3 MPa, the superheated steam S blasted to the preform may be condensed on the surface thereof. When the steam is condensed, there is a fear of generating whitening or like on the surface of a bottle at the time when the preform is blow-molded into the bottle.

Furthermore, it is preferred that the time for blasting the superheated steam S to the preform 1 is within 1.0 to 10.0 sec. In the case of less than 1.0 sec., defective sterilization may be likely caused, and in the case of more than 10.0 sec., the mouth portion 1a of the preform 1 may be likely deformed. This superheated steam blasting time can increase the sterilizing effect by the superheated steam S because the surface of the preform 1 is preliminarily heated as mentioned hereinbefore in comparison with the case in which the preheating is not effected, and as a result, the superheated steam blasting time can be reduced and less energy consumption can be performed.

The superheated steam S is discharged in a direction crossing the conveyor 4 from both sides of the conveyor 4 within the second chamber 6a, and since the preform 1 is overturned on the conveyor 4 by vibration or like, the superheated steam S uniformly contacts the surface of the preform 1. At the same time, the superheated steam S flows inside the overturned preform through the mouth portion 1a thereof, and thus, superheated steam S uniformly contacts the inner surface of the preform 1. Moreover, since the superheated steam S discharged from the sterilization nozzle 60 fills and circulates in the second chamber 6a, this superheated steam S also uniformly adheres to the surface of the preform 1. Thus, the entire surface of the preform 1 is suitably sterilized by the superheated steam S.

The superheated steam S discharged into the second chamber 6a is sucked into the exhaust duct 61 by the operation of the blower, not shown, and then discharged out of the second chamber 6a.

The superheated steam S can be obtained by using a commercially sold superheated steam generator 62 shown in FIG. 10(B). By guiding water into a water-pass pipe and by applying the A.C. voltage to the induction heating coil, the water-pass pipe is heated. The heat generation of the water-pass pipe causes the water to be saturated steam state, which is then converted into the superheated steam S, which is thereafter taken out of the water-pass pipe.

According to the superheated steam generator 62 of the structure mentioned above, it is possible to obtain a superheated steam as the superheated steam S having a pressure of 0.1 MPa and a temperature of 200 to 700° C. By adopting the induction heating method mentioned above, the water can be converted into the superheated steam S having the temperature of more than 200° C. for a short time from the conduction-start time. This superheated steam S is taken out from the tip end of the conduit 63 connected to the terminal end of the water-pass pipe of the superheated steam generator 62 and then distributed to the respective sterilization nozzles 60.

The downstream side furtherer than the second chamber 6a of the conveyor 4 extends toward a large container, not shown. The preform 1 sterilized within the second chamber 6a by the superheated steam S is transferred toward and then into the large container by the conveyor 4. This large container is sealed and stored after the accommodation of predetermined numbers of the preforms, and then transferred to a factory in which the preforms are molded into bottles.

Further, in an arrangement in which the downstream side furtherer than the second chamber 6a of the conveyor 4 is connected to the blow-molding machine, the sterilized preform 1 is immediately blow-molded into a container such as bottle. Moreover, in an arrangement in which the blow-molding machine is connected to the content filling machine, the container such as bottle is filled with a content such as drink, sealed and then discharged as the aseptic package of products.

Example 5

The first chamber 5a and the second chamber 6a have a size of 1000 mm width, and 1500 mm length, and 200 mm height, respectively. Preforms, each being formed into a bottle of 500 ml, were supplied to the conveyor by the number of 860 bottles/min., and the conveyor was driven at a predetermined speed. In this operation, the temperature of the hot air H in the first chamber 5a, and the blasting temperature of the superheated steam S in the second chamber 6a, and the concentration of the hydrogen peroxide were set as shown in the Table 5, which also shows obtained sterilization results.

TABLE 5

| Hot Air Temperature In First Chamber (° C.) | Superheated Steam Blasting Temperature In Second Chamber (° C.) | Travelling Speed (m/sec.) | B. sub. | A. niger |
|---|---|---|---|---|
| 100 | 300 | 0.2 | 2.2D | 5.0D |
| 100 | 500 | 0.2 | 2.8D | 6.0D |

TABLE 5-continued

| Hot Air Temperature In First Chamber (° C.) | Superheated Steam Blasting Temperature In Second Chamber (° C.) | Travelling Speed (m/sec.) | B. sub. | A. niger |
|---|---|---|---|---|
| 100 | 500 | 0.5 | 2.0D | 5.0D |
| 130 | 500 | 0.2 | 3.0D | More Than 6.0D |
| 100 | 700 | 0.2 | 3.1D | More Than 6.0D |
| NO | 500 | 0.2 | 1.0D | 3.0D |
| 50 | 500 | 0.2 | 1.8D | 3.5D |

In the above Table 5, term "B.sub." is an abbreviated term of "BaciLLus subtiLis", and "A.nig." is an abbreviated term of "AspergiLLus niger". "D" is a D-valve indicating the sterilizing effect.

As is apparent from the above Table 5, in the case where the preform was not preheated, the sterilizing effect was 3.0 D with respect to the *A. niger*, but in the case where the preform was preheated by blasting the hot air, the sterilizing effect more than 6.0 D with respect to the *A. niger* could be obtained without increasing the superheated steam temperature or increasing the blasting amount thereof.

REFERENCE NUMERAL

1—preform
1a—mouth portion of preform
4—conveyer
5—chamber
5a—first chamber
6a—second chamber
10—spray nozzle
51—preheating nozzle
60—sterilization nozzle
H—hot air
M—hydrogen peroxide water mist
S—superheated steam

The invention claimed is:

1. A method for sterilizing a preform, comprising the steps of:
   loading a number of preforms, each having a bottomed tubular shape, on a conveyer in an irregular lying state,
   while the preforms are arranged in the irregular lying state on the conveyer, passing the preforms through a chamber together with the conveyer, and
   spraying hydrogen peroxide water to the preforms, while the preforms are being overturned on the conveyer by vibration, within the chamber from both sides of the conveyer in a direction crossing the conveyer, thereby adhering the hydrogen peroxide water to inner and outer surfaces of each of the preforms that are arranged in the irregular lying state on the conveyer.

2. The preform sterilizing method according to claim 1, wherein the hydrogen peroxide water is atomized into a mist by a two-fluid spray using pressurized air.

3. The preform sterilizing method according to claim 2, wherein hot air having a temperature of 40° C. to 150° C. is mixed with the mist of the hydrogen peroxide water.

4. The preform sterilizing method according to claim 2, wherein a concentration of the hydrogen peroxide water is within 20% to 35%.

5. The preform sterilizing method according to claim 2, wherein hot air having a temperature of 40° C. to 150° C. is mixed with the mist of the hydrogen peroxide water.

6. The preform sterilizing method according to claim 1, wherein a concentration of the hydrogen peroxide water is within 20% to 35%.

7. The preform sterilizing method according to claim 1, wherein an interior of the chamber is preliminarily sterilized by spraying the hydrogen peroxide water before starting the sterilization of the preform.

* * * * *

UNITED STATES PATENT AND TRADEMARK OFFICE
CERTIFICATE OF CORRECTION

PATENT NO. : 10,548,999 B2  
APPLICATION NO. : 14/384697  
DATED : February 4, 2020  
INVENTOR(S) : Yoshihiro Miyahara, Hirotaka Tsuchiya and Yoshio Nishida Page 1 of 1

It is certified that error appears in the above-identified patent and that said Letters Patent is hereby corrected as shown below:

On the Title Page

Assignee, Item (73)
Please change: "Assignee: Sai Nippon Printing Co., Ltd., Shinjuku-Ku (JP)" to
-- Assignee: Dai Nippon Printing Co., Ltd., Shinjuku-Ku (JP) --

Signed and Sealed this  
Twenty-fourth Day of March, 2020

Andrei Iancu  
*Director of the United States Patent and Trademark Office*